US011369399B2

(12) United States Patent
Bagwell et al.

(10) Patent No.: US 11,369,399 B2
(45) Date of Patent: Jun. 28, 2022

(54) DEVICE FOR AIDING IN THE POSITIONING AND ANCHORING OF AN ENDOSCOPE DURING GASTROINTESTINAL PROCEDURES

(71) Applicant: Actuated Medical, Inc., Bellefonte, PA (US)

(72) Inventors: Roger B Bagwell, Bellefonte, PA (US); Timothy J Higgins, Mingoville, PA (US); Eric J Hopkins, Bellefonte, PA (US); Casey A Scruggs, Bellefonte, PA (US); Kevin A Snook, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 646 days.

(21) Appl. No.: 16/034,965

(22) Filed: Jul. 13, 2018

(65) Prior Publication Data
US 2019/0015125 A1    Jan. 17, 2019

Related U.S. Application Data

(60) Provisional application No. 62/532,508, filed on Jul. 14, 2017.

(51) Int. Cl.
*A61B 1/00* (2006.01)
*A61B 1/015* (2006.01)
(Continued)

(52) U.S. Cl.
CPC ............ *A61B 17/30* (2013.01); *A61B 1/0014* (2013.01); *A61B 1/00087* (2013.01);
(Continued)

(58) Field of Classification Search
CPC ............ A61B 1/00087; A61B 1/00089; A61B 1/00094; A61B 2017/00477;
(Continued)

(56) References Cited

U.S. PATENT DOCUMENTS

| 5,549,627 A | 8/1996 | Kieturakis |
| 5,766,215 A | 6/1998 | Muri |

(Continued)

FOREIGN PATENT DOCUMENTS

| JP | 5775989 B1 | 9/2015 |
| WO | WO2017070183 A1 | 4/2017 |

OTHER PUBLICATIONS

International Searching Authority; International Search Report and Written Opinion of the International Searching Authority; International Application No. PCT/US2014/34017; Patent Cooperation Treaty; pp. 1-12; publisher United States International Searching Authority; Published Alexandria, Virginia, US; copyright and dated Jun. 1, 2015; (12 pages).

(Continued)

*Primary Examiner* — Aaron B Fairchild
(74) *Attorney, Agent, or Firm* — Metz Lewis Brodman Must O'Keefe LLC

(57) ABSTRACT

A device for engaging tissue includes a body disposable around the distal end of a medical instrument, such as an endoscope, and a handpiece. The body includes a primary channel for receiving the medical instrument and at least one arm channel for receiving an arm therethrough. At least one arm extends through the arm channel of the body and proximally to the handpiece. The arm includes an engagement member distally of the body, and may further include a bend between the body and engagement member. The engagement member is movable between a first position not contacting tissue and a second position contacting tissue.

(Continued)

With multiple engagement members, the engagement members are farther apart from one another in the first position and closer together in the second position. Movement of the engagement members is controlled by selective and independent movement of the corresponding arms by rotational and/or translational motion.

23 Claims, 15 Drawing Sheets

(51) Int. Cl.
    *A61B 17/30*     (2006.01)
    *A61B 17/29*     (2006.01)
    *A61B 17/00*     (2006.01)
    *A61B 17/02*     (2006.01)

(52) U.S. Cl.
    CPC ...... *A61B 1/00089* (2013.01); *A61B 1/00094* (2013.01); *A61B 1/015* (2013.01); *A61B 17/0218* (2013.01); *A61B 2017/00269* (2013.01); *A61B 2017/00296* (2013.01); *A61B 2017/00367* (2013.01); *A61B 2017/00477* (2013.01); *A61B 2017/00818* (2013.01); *A61B 2017/2901* (2013.01); *A61B 2017/2926* (2013.01); *A61B 2017/305* (2013.01); *A61B 2217/005* (2013.01); *A61B 2217/007* (2013.01)

(58) Field of Classification Search
    CPC .............. A61B 1/00137; A61B 1/0014; A61B 1/00149; A61B 1/0016; A61B 2017/00367
    See application file for complete search history.

(56) References Cited

U.S. PATENT DOCUMENTS

| | | | |
|---|---|---|---|
| 5,876,325 A * | 3/1999 | Mizuno | A61B 1/00188 600/102 |
| 8,100,900 B2 | 1/2012 | Prinz | |
| 9,596,980 B2 | 3/2017 | Marescaux et al. | |
| 2005/0256524 A1 | 11/2005 | Long | |
| 2006/0161045 A1* | 7/2006 | Merril | A61B 34/70 600/117 |
| 2008/0021499 A1* | 1/2008 | Miyamoto | A61B 17/062 606/206 |
| 2008/0221504 A1 | 9/2008 | Aghion | |
| 2008/0269562 A1* | 10/2008 | Marescaux | A61B 1/00087 600/142 |
| 2009/0281534 A1 | 11/2009 | Prinz | |
| 2009/0287043 A1* | 11/2009 | Naito | A61B 1/00133 600/104 |
| 2009/0306541 A1 | 12/2009 | Kano | |
| 2010/0010492 A1 | 1/2010 | Lockard | |
| 2011/0087266 A1 | 4/2011 | Conlon | |
| 2011/0270241 A1 | 11/2011 | Boutoussov | |
| 2012/0022532 A1 | 1/2012 | Garrison | |
| 2012/0035606 A1 | 2/2012 | Kano | |
| 2013/0012975 A1 | 1/2013 | Schmitz | |
| 2013/0066297 A1 | 3/2013 | Shtul et al. | |
| 2014/0012287 A1 | 1/2014 | Oyola et al. | |
| 2016/0278626 A1 | 9/2016 | Cornhill et al. | |
| 2017/0332882 A1* | 11/2017 | Yamamoto | A61B 1/005 |

OTHER PUBLICATIONS

Burrows, Leah; Smaller, smarter, softer robotic arm for endoscopic surgery; https://wyss.harvard.edu/smaller-smarter-softer-robotic-arm-for-endoscopic-surgery/, Aug. 2, 2017 pp. 1-11; (11 pages).
Medrobotics website; https://medrobotics.com/; Sep. 19, 2018; 2 pages.
Pentax Medical website; http://www.the-hygiene-solution-that-fits.com/products/dec-duodenoscope/; 11 pages.
UK Intellectual Property Office, Examination Report under Section 18(3) regarding UK Application No. GB2001844.6; pp. 1-5, publisher UK Intellectual Property Office, published South Wales, NP, copyright and dated Dec. 10, 2021; (5 pages).
Japanese Patent Office; Office Action; Office Action regarding Japanese Patent Application No. 2020-501493; pp. 1-6; publisher Japanese Patent. Office; published Tokyo, Japan; copyright and dated Apr. 11, 2022 copy enclosed (6 pages).

* cited by examiner

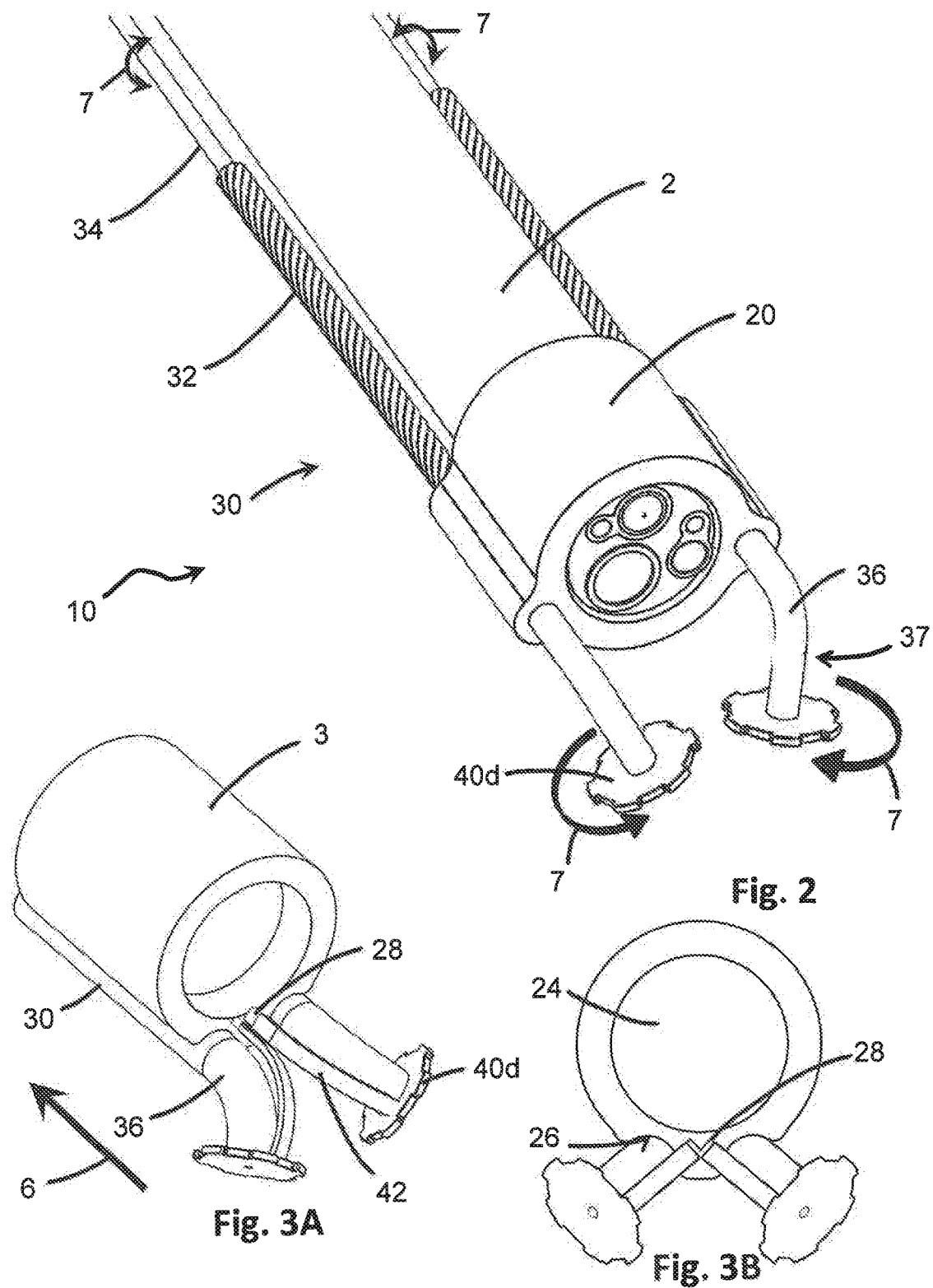

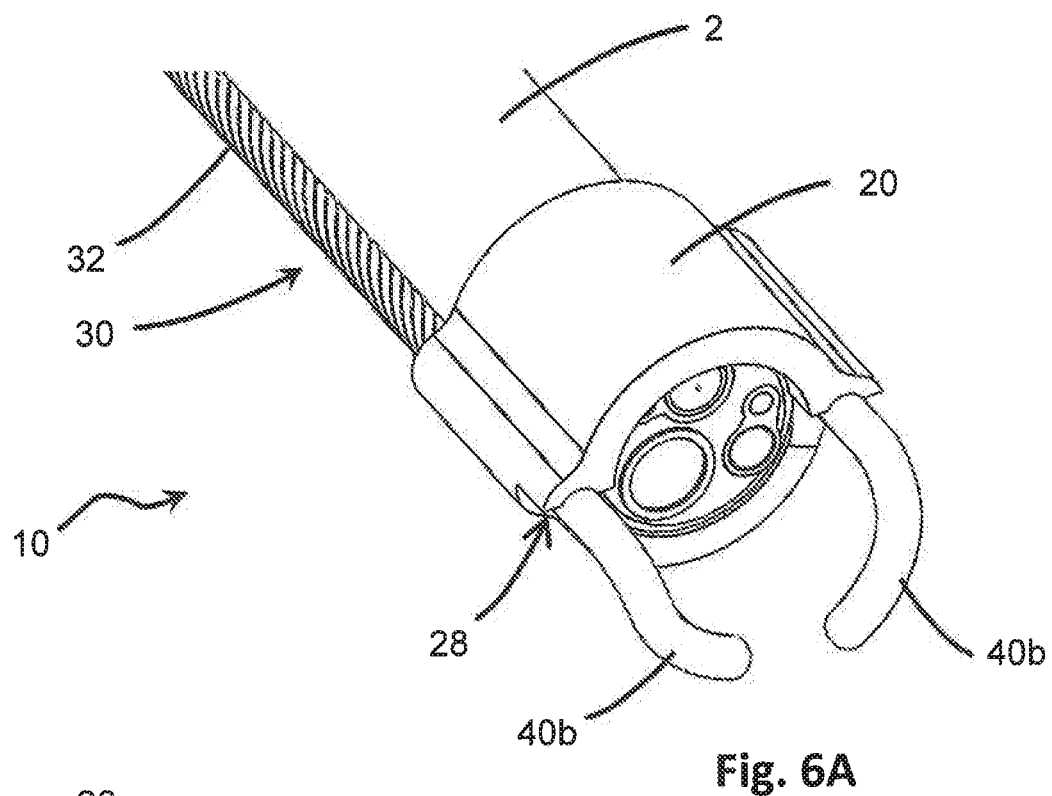
Fig. 6A
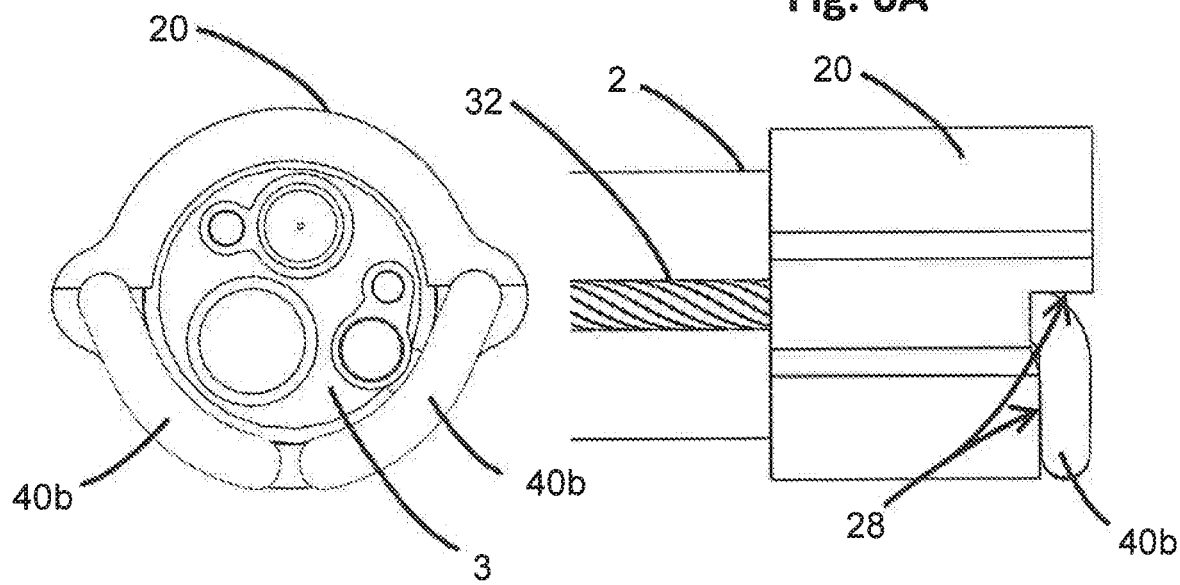
Fig. 6B
Fig. 6C

DEVICE FOR AIDING IN THE POSITIONING AND ANCHORING OF AN ENDOSCOPE DURING GASTROINTESTINAL PROCEDURES

CLAIM OF PRIORITY

The present application which claims priority to U.S. Provisional Application Ser. No. 62/532,508 filed on Jul. 14, 2017, the contents of which is incorporated herein by reference in its entirety.

STATEMENT REGARDING FEDERALLY SPONSORED RESEARCH OR DEVELOPMENT

This invention was made with government support under 1353176 awarded by the National Science Foundation and DK117813 awarded by the National Institutes of Health. The government has certain rights in the invention.

FIELD OF THE INVENTION

This invention relates to a device for engaging tissue, and more particularly, to a device for gripping, holding and manipulating tissue during an internal procedure which does not obstruct the working end of a medical instrument to which it is attached.

BACKGROUND

Identification and treatment of diseases and damage within the gastrointestinal (GI) system represent a major sector of healthcare. It is estimated that in the United States alone, inpatient care for acute GI bleeding and colorectal cancer are more than $2.5 billion and $5.5 billion, respectively, with a combined annual mortality rate of nearly 80,000. Identification of pathologies and intervention are generally treated through minimally invasive methods using endoscopic techniques and devices. In 2009, it was estimated that more than 55 million endoscopic procedures were performed with endoscopic devices, and nearly 50% of those were for colonoscopies.

Endoscopes are minimally invasive devices that allow physicians access to the GI system via naturally occurring orifices (i.e., mouth or rectum) for diagnostic and/or intervention or therapy. Endoscopes are generally flexible tubes of up to two meters in length, which incorporate deflection capability, optical or digital viewing, and several internal channels, including irrigation, illumination, and one or two "working" channels. The direct engagement with internal organs enables localized diagnostics or interventions with minimal collateral damage to surrounding tissues relative to open surgery, but is limited in viewing capability and instrument control, which is a root cause of many missed diagnoses and incomplete treatments.

Traversing the GI system is challenging due to the convoluted paths, the elasticity of tissues, and the surface topology of the mucosal surface. In the lower GI tract, the haustral folds, which can be up to 1 cm in height, can often hide lesions from the colonoscope as it is retracted. This is because it is necessary for the scope to retract past a region before it is viewable. Once the scope is retracted past this point, the scope no longer holds down the haustral fold, which can flip back and hide the region just anterior to the fold. This can result in the physician missing detection of lesions in this region. Depending on the size or type of lesion, miss rates as high as 21-31% have been reported, which corresponds to nearly 500,000 missed diagnoses per year. Additionally, biopsies and interventions are similarly affected, and interventions can be forced into an open procedure, increasing risks of infection and complications from general anesthesia.

GI bleeds result from damage to the tissue and are among the most challenging GI conditions to treat because of the convoluted path to the treatment area, visual obstruction of the target by the hemorrhage, and disruption of continuous treatment due to physiological motion (i.e., respiration and peristalsis) of the patient. Re-bleeding can occur when these obstacles result in limited maneuverability of the endoscope, insufficient treatment time for permanent hemostasis, and inaccurate placement of the treatment at the target. Though bleeding is stopped temporarily, re-bleeding and recurrent re-bleeding can occur at a later time, and result in additional surgical time and increased readmission rates. Re-bleed affects 15-20% of patients and also increases the risk of mortality by ten-fold.

Several new technologies and techniques have developed to address the inadequate detection of GI diseases and damage. For instance, the angle of view of endoscopes has increased from 90 degrees to 140 degrees, and recently to 170 degrees, to decrease the amount of surface tissue that is not viewable by the endoscope. Retroversion and retroflexion have both been employed to bend or turn the endoscope backward within the GI tract for viewing in the reverse direction, and a separate retroscope has been developed to advance through the working channel of a colonoscope and provide retrograde viewing of the colon. However, use of the working channel for this purpose reduces treatment capability since only one tool can be used in the working channel at a time. Tools can be interchanged, but visualization is lost and the endoscope can drift and lose location. Further, maintaining position during procedures with these medical instruments is extremely difficult due to patient movement, peristalsis of the GI tract, and other bodily movements. Clinicians often spend several minutes searching for their lost target—reducing the accuracy and effectiveness of detection, diagnosis and treatment.

A device is therefore needed that can grasp and manipulate tissue, navigate to a bleed, and hold position while a procedure is performed, without negatively impacting the procedure or tissue or requiring the use of a working channel of an endoscope.

SUMMARY

The present invention relates generally to a device that can be used to engage tissue within a patient such as for tissue gripping and manipulation, which may be used to aid in the positioning and anchoring of the distal end of a medical instrument, such as an endoscope. The device can be releasably attached to the endoscope in a manner that does not interfere with the working channel(s) of the endoscope so a clinician can still have full use of the working channel(s) of the endoscope.

Once the general target area within the GI tract has been achieved through standard maneuvering and macro-positioning, the present device can be used to manipulate and grip tissue to make small adjustments in the endoscope position or to move tissue. This additional control provided by the device is beneficial in various GI procedures such as polyp removal, GI bleed repairs, and tissue sectioning. For instance, with the present device, tissue may be moved so that it is not obstructing the lens of the endoscope, to better visualize the tissue and/or lesions thereon, so the clinician may move haustral folds or other biological structures out of the way of the device being deployed through the working channel, or so that tissue can be grasped and retracted during biopsy procedures.

The additional contact and/or gripping afforded by the present invention can also be used to maintain the position or anchoring of the distal end of the endoscope, thereby overcoming peristalsis and other muscular contractions such as breathing that could otherwise hinder the clinical procedure or lead to lost time in repositioning the endoscope.

Accordingly, the device includes a body at a distal end and a handpiece at a proximal end. The body includes a primary channel configured to receive the distal end of a medical instrument, such as an endoscope. The body may be at least partially circumferentially disposed about the exterior surface of the working end of an endoscope. The device therefore does not obstruct the working end of the endoscope or the additional medical instruments used therein.

The body also includes at least one arm channel configured to receive an arm therethrough. Preferably, there are two or more arms and each arm extends through a different arm channel in the body. The arms extend from the distal end of the device to the handpiece at the proximal end of the device. Each arm terminates in an engagement member at the distal end of the device and distally of the body. The engagement member is configured to engage tissue, such as for manipulation, gripping, anchoring, etc. The engagement member may be rigidly fixed to or integrally formed with the end of the arm. Each arm may also include a bend, such as an elbow, that changes the direction or angle of the engagement member from the axis of the arm.

Each of the arms is selectively movable relative to the body independently of the other arm(s). For instance, each arm may be rotated by rotational motion about the longitudinal axis of the arm. Each arm may also be moved longitudinally in a distal or proximal direction, collectively referred to as translational motion. As each arm moves, the attached engagement member also moves. However, because the bend or elbow shifts the engagement member to be non-axial relative to the corresponding arm, the rotational motion of the arm may move the attached engagement member in a lateral direction that is transverse to the axis of the arm. This lateral direction may include an arcuate path.

Movement of the arms moves the corresponding engagement members between first and second positions. In the first position, the engagement members are not contacting tissue, and may be considered an open position. In the second position, at least one of the engagement members is contacting tissue. Further, the distance between engagement members in the second position is less than when in the first position. Accordingly, the second position may be referred to as a closed position. The closed position may be achieved by moving the arm(s) with rotational motion, translational motion, or a combination of both. The distance between the engagement members may be decreased in either the lateral direction (i.e., transverse to the axis of the arms) or in the longitudinal direction. As the engagement members are brought closer together, the force they assert on the contacted tissue increases. The engagement members may therefore grip, pinch, collect, hold or otherwise retain tissue therebetween in the second position. With enough force, the engagement members may grip or hold the tissue sufficiently tightly that they anchor the attached endoscope to that location, thus preventing drift or losing the target site during the medical procedure. The contact of the engagement members with the tissue is releasable. When desired, the reverse motion may be applied to the arms to move the engagement members to a first position, thereby releasing the tissue.

The handpiece at the proximal end of the device includes the controls for operating the arms. The handpiece includes an actuator and at least one of a rotational adjustment mechanism and/or a translational adjustment mechanism. The actuator may be activated, such as by rotating, turning or sliding, which subsequently moves the components of the rotational adjustment mechanism and/or a translational adjustment mechanism depending on which adjustment mechanism is engaged with the actuator or the manner in which the actuator is activated.

In some embodiments, one or more arms may be hollow and include a lumen extending in fluid communication through the engagement member at the distal end and a connector for attaching to a fluid reservoir at the proximal end. Irrigation and/or aspiration may be provided through the fluid reservoir, and thus through the hollow arm and corresponding engagement member. Accordingly, the device may provide irrigation and/or aspiration without tying up working channels of the endoscope.

The device, together with their particular features and advantages, will become more apparent from the following detailed description and with reference to the appended drawings.

DESCRIPTION OF THE DRAWINGS

FIG. 2 is an isometric schematic diagram of a second embodiment of the distal end of the device of the present invention in connection with the distal end of an endoscope, where the device includes gear-shaped engagement members.

FIG. 3A is an isometric schematic diagram of a third embodiment of the distal end of the device, showing spring arms connected to the engagement members.

FIG. 3B is an end elevation view of the device of FIG. 3A.

FIG. 6A is an isometric schematic diagram of a sixth embodiment of the distal end of the device in connection with the distal end of an endoscope, where the engagement members are rounded.

FIG. 6B is an end elevation of the distal end of the device of FIG. 6A.

FIG. 6C is a side elevation of the distal end of the device of FIG. 6B, showing the engagement members stowed within a recess of the device body.

Like reference numerals refer to like parts throughout the several views of the drawings.

DETAILED DESCRIPTION

As shown in the accompanying drawings, the present invention is directed to a device 10 that can be fitted to a medical instrument, such as an endoscope 2, to assist with positioning and anchoring the medical instrument 2 to target tissue during a medical procedure. For instance, FIGS. 1A-7 show the distal end 12 of the device 10 for use in connection with the distal end of a medical instrument, such as an endoscope 2 shown here, which can be inserted into a patient and navigated to an internal location such as within the GI tract for diagnosis and/or treatment. As used herein, "distal" refers to the end that is closest to or inserted into the patient, and "proximal" refers to the end closest to the clinician or user of the device 10.

Figure 1A:
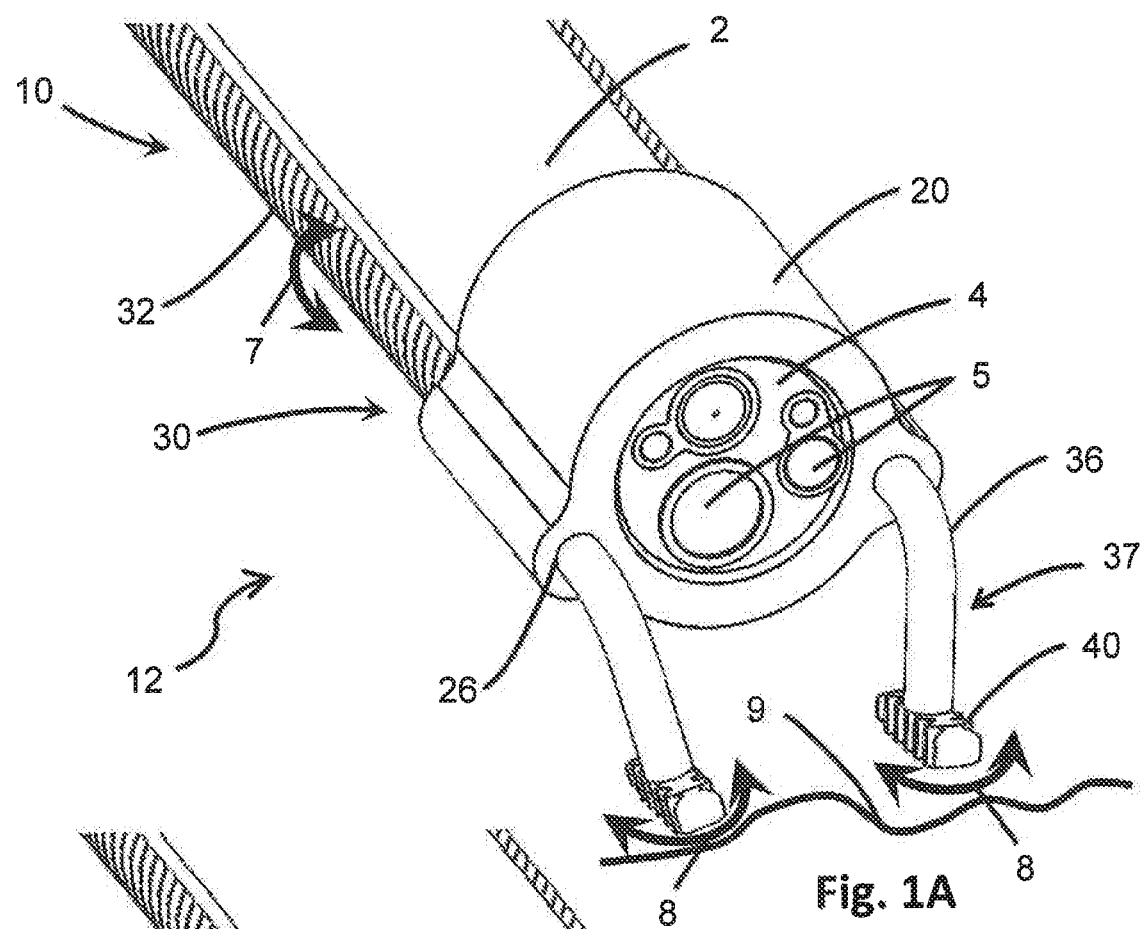
FIG. 1A is an isometric schematic diagram of one embodiment of the distal end of the device of the present invention in connection with the distal end of an endoscope.

The device 10 includes a body 20 that is configured to selectively attach to a medical instrument, such as an endoscope 2. The body 20 may be made of a rigid or semi-rigid material such as stainless steel, titanium, polycarbonate, polyetherimide, silicone or any other biocompatible material which provides sufficient rigidity to hold its form but may also be flexible or resilient in certain areas to allow for attachment to the endoscope 2. As shown in FIGS. 1A-2 and 5A-7, the body 20 may be configured to be at least partially circumferentially disposed about the working end 3 of an endoscope 2, located at the distal end thereof. For instance, the body 24 may include a primary channel 24 extending through the length of the body 20, and which is dimensioned to accommodate the working end 3 of an endoscope 2. The primary channel 24 may have any diameter as permits receiving and restraining a portion of the medical instrument, such as endoscope 2, therethrough. For instance, the primary channel 24 may have a diameter that is substantially similar to, or slightly larger than, the diameter of the outer surface of the endoscope 2, such that the body 20 may secure to the endoscope 2 by a frictional fit therewith. In some embodiments, as seen in FIGS. 1A-2, the body 20 may entirely circumferentially surround the outer surface of the working end 3 of an endoscope 2. In such embodiments, the working end 3 of an endoscope 2 may be passed through the primary channel 24 of the body 20 of the device 10 until the body 20 and the endoscope 2 frictionally engage one another with sufficient force to remain stationary relative to one another. Preferably, this may occur when the end of the body 20 is co-terminal with the face 4 of the working end 3 of the endoscope 2. The frictional fit between the body 20 and endoscope 2 may be released when desired by applying force to the body 20 in a distal direction in order to pass the working end 3 of the endoscope 2 through the primary channel 24 in the reverse order. In other embodiments, the body 20 may only partially circumferentially surround the endoscope 2 when attached. For instance, the body 20 may be C-shaped or otherwise shaped to attach with a snap-fit engagement to the endoscope 2.

Figure 7:
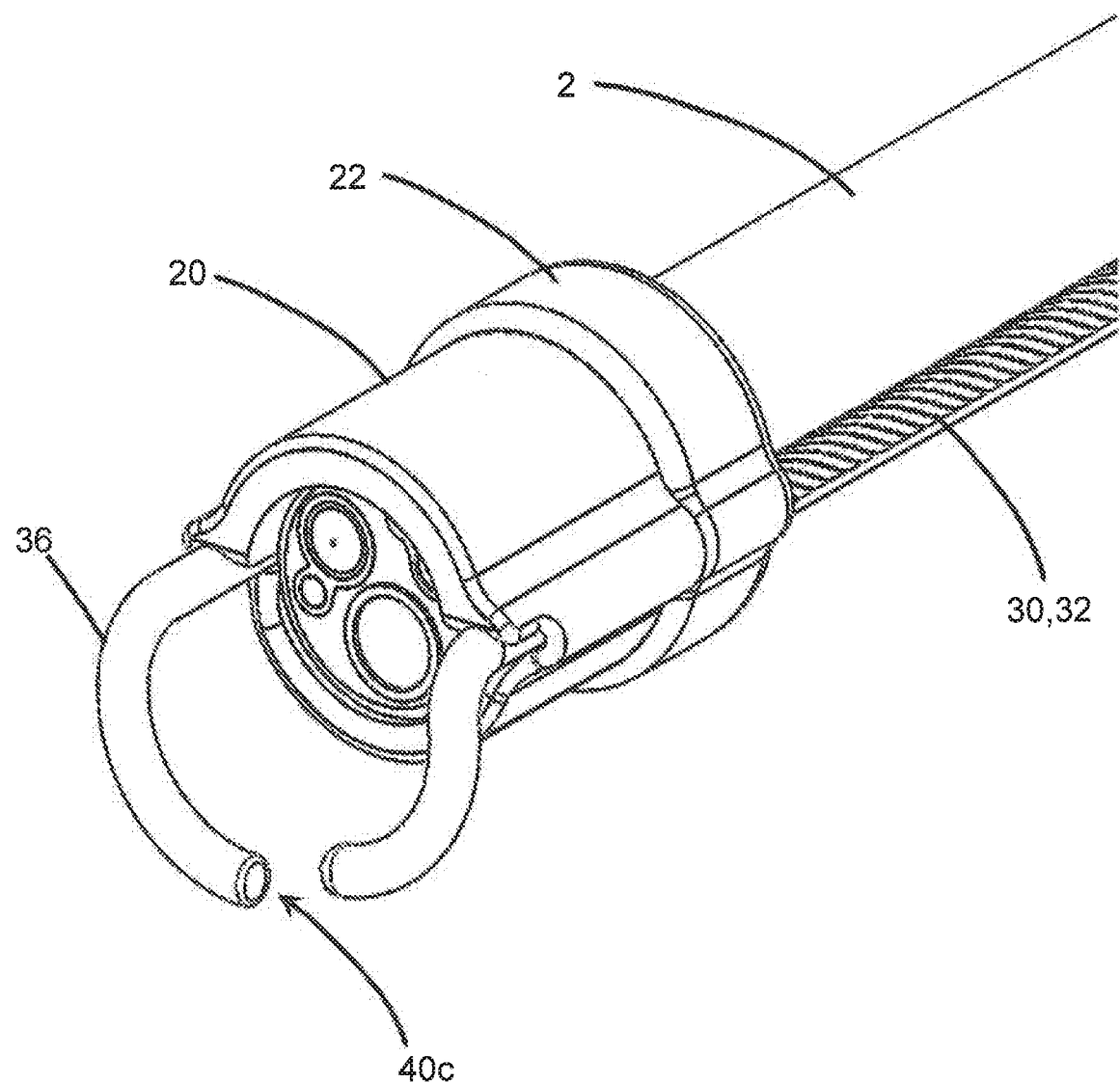
FIG. 7 an isometric schematic diagram of a seventh embodiment of the distal end of the device in connection with the distal end of an endoscope, where the engagement members are rounded and one engagement member includes a lumen extending therethrough.

In some embodiments the device 10 may also include a clip 22, as shown in FIG. 7, which may attach to one or both the body 20 and endoscope 2 to secure them together. For instance, the clip 22 may be a collar or other circumferentially disposed component that may attach to and restrain the body 20 with sufficient force against the endoscope 2 that it secures the body 20 to the endoscope 2. In some embodiments, the clip 22 may overlap a portion of the body 20 and a portion of the endoscope 2 in providing restrictive force to secure them together. The clip 22 may attach with a snap-fit engagement, or may be circumferentially disposed around the body 20 and/or endoscope 2 and tightened, such as by a threaded bolt, screw, wingnut or other suitable selective tightening mechanism that can later be removed when desired. In certain embodiments, the clip 22 may also fasten a sterile sleeve (not shown) surrounding the length of the endoscope 2 to the device 10.

Regardless of the mechanism of attachment, the body 20 attaches to the endoscope 3 in a manner that does not interfere with the working end 3 of the endoscope 2. As shown in FIGS. 1A-2 for example, with the body 20 circumferentially disposed around the outer surface of the endoscope 2, the entire face 4 of the working end 3 remains exposed. The various working channels 5 of the endoscope 2 are not obstructed by the device 10. No part of the device 10 uses or need interact with any of the working channels 5 of the endoscope 2, leaving the working channels 5 free to be used by a clinician or operator of the endoscope 2 for various tools, lights, imaging devices, and irrigation as may be required for a particular procedure.

The body 20 may also include at least one, but preferably a plurality of arm channels 26 each extending through the body 20. In at least one embodiment, as in FIGS. 1A-3, the arm channels 26 may extend along the length of the body 20, and may be parallel to the primary channel 24. In other embodiments, as in FIG. 4B, the arm channels 26 may include any number of turns, curves, angles, or other features that may deviate the arm channel 26 from a linear path. In many embodiments, the arm channels 26 may have a diameter that is fully disposed within the body 20 of the device 10, as in FIGS. 1A-2. In other embodiments, as in FIGS. 3A-3B, the arm channels 26 may be formed in the outer surface of the body 20 such that they have a partial diameter. Regardless of position, each arm channel 26 may have a diameter less than that of the primary channel 24 through which the endoscope 2 fits, although in some embodiments the diameter of the arm channels 26 may be equivalent to or larger than the primary channel 24. Further, the arm channels 26 may have the same or different diameters compared to one another. There may also be any number of arm channels 26, although preferably the body 20 includes two arm channels 26. The arm channels 26 may be disposed equidistant from one another in the body 20, or may be spaced closer together or further apart from one another. However, the position of the arm channels 26 within the body 20 are preferably fixed.

The device 10 further includes at least one, but preferably two or more arms 30 each extending through a different one of the arm channels 26 of the body 20. Each arm 30 is elongate, extending along the length of the endoscope 2 and is sufficiently flexible to bend, flex and twist along with the endoscope 2 during the movement of the endoscope 2 through the GI tract to the target site. Accordingly, the arms 30 may be parallel to the endoscope 2 over some, if not most, of the length of the endoscope 2 between the working end 3 and the proximal end where entry into the patient is made. The arms 30 may therefore be flexible, and made of material such as but not limited to nitinol or stainless steel. Each arm 30 may further include a bend 36 located distally from the body 20 of the device 10. The bend 36 may be a curve, angle or elbow that changes the direction of the arm 30 so that a portion of the arm 30 which extends beyond the face 4 of the working end 3 of the endoscope 2 is no longer parallel to the endoscope 2. For instance, the bend 36 may introduce a change in the direction of the arm 30 by up to 180°. Each arm 30 may also include a forearm 37 defined between the bend 36 and the terminal end of the arm 30. The forearm 37 may preferably be linear, but can have any configuration. Because of the change in angle from the bend 36, the forearms 37 of the arms 30 are positionable closer to and further apart relative to one another without having the change the position of the remainder of the arms 30 or the arm channels 26 through which they are disposed. In some embodiments, the arm 30, bend 36 and forearm 37 are all integrally formed, such that the bend 36 and forearm 37 are portions of the arm 30. In certain embodiments, the bend 36 and/or forearm 37 may be made of a different material than that of the arm 30, and may be attached to the arm 30. For instance, the bend 36 and/or forearm 37 may be made of a more rigid material than that of the arm 30, where the arm 30 is sufficiently flexible to bend and flex through the GI tract and the bend 36 and/or forearm 37 are sufficiently rigid to transfer motion. In some embodiments, the bend 36 and/or forearm 37 may be securely attached to the arm 30 so that they are not removable therefrom. In other embodiments, one or both the bend 36 and/or forearm 37 may be removably attached to the arm 30, so different angles or materials may be selected for different procedures.

Figure 1B:
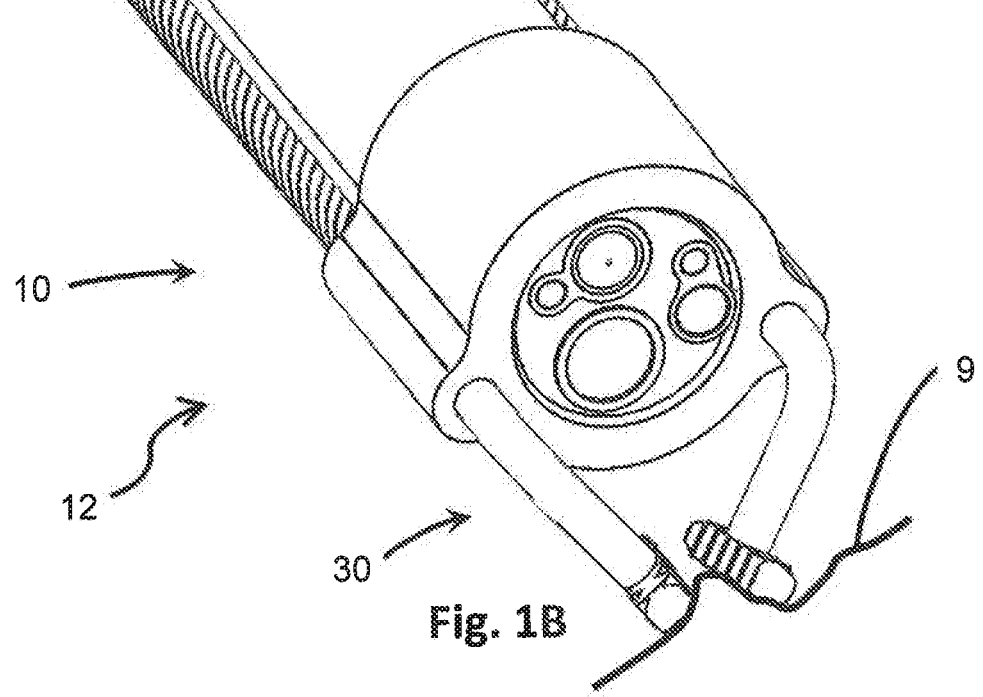
FIG. 1B is an isometric view of the device of FIG. 1A, showing the engagement members coordinating in a lateral direction to grip tissue.
Figure 1C:
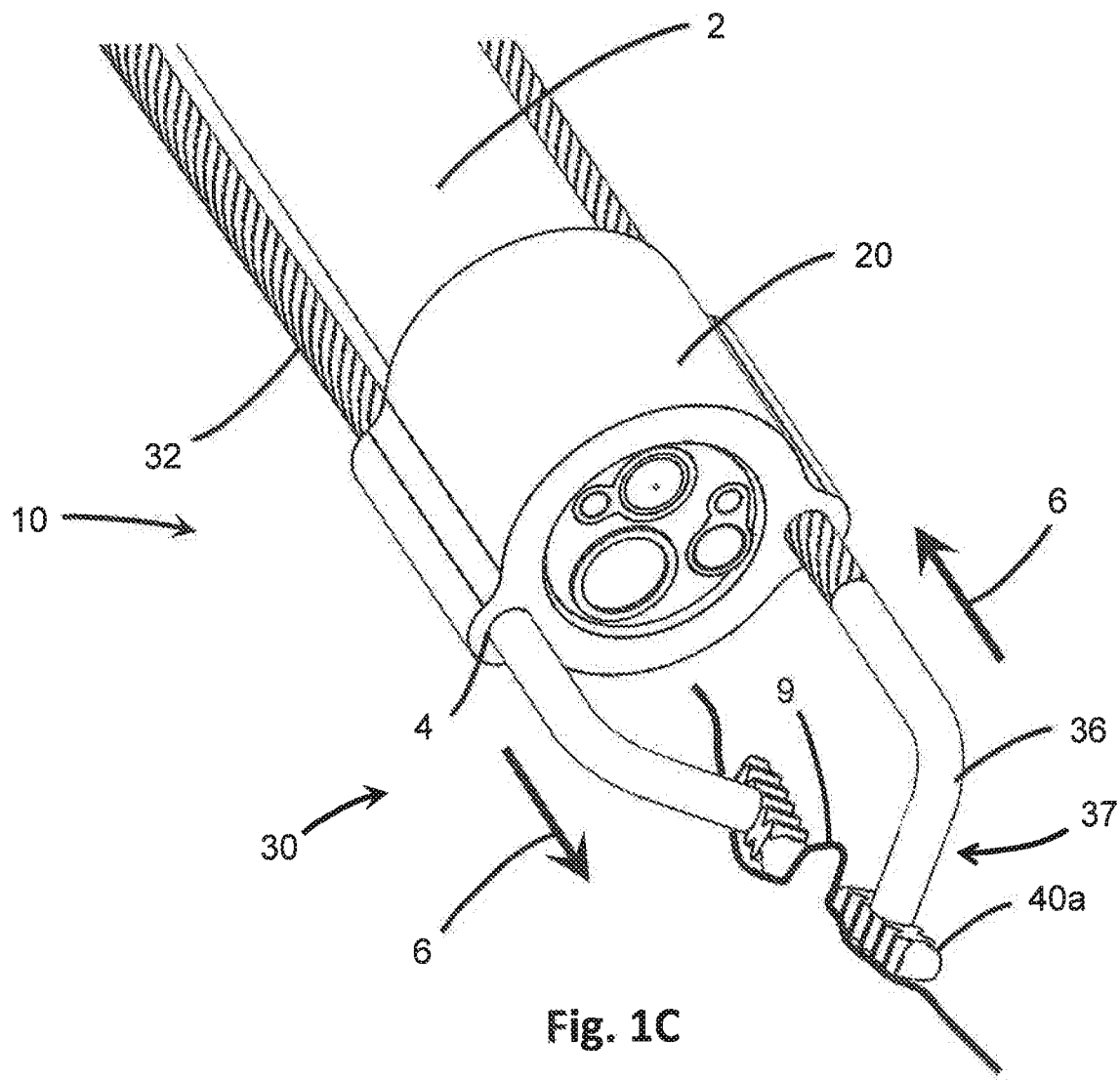
FIG. 1C is an isometric view of the device of FIG. 1A, showing the engagement members coordinating in a longitudinal direction to grip tissue.

In at least one embodiment, the arms 30 may be configured to accept rotation and convey torque along their length such as from a proximal end to the distal end of the device 10. For instance, the arms 30 may be rotated about their longitudinal axis and relative to the body 20 from a proximal end by a clinician. The torque applied from the rotation is propagated through the length of the torque wire, even to the distal end, such that the distal end is also rotated by such torque. Each arm 30 may be rotated by a clinician separately and independently of the other arm(s) 30 of the device 10, or may be rotated simultaneously if desired. In at least one embodiment as seen in FIGS. 1A-1C, the arms 30 may be defined as a torque transmission member 32, which may be a stranded torque wire or a helical hollow stranded torque wire of with an inner diameter in the range of about 0.003-0.080 inch and an outer diameter in the range of about 0.006-0.100 inch. Torque wires are designed to be flexible so they can bend and flex through tortuous pathways, which may be ideal for intravascular and percutaneous routes such as in GI tract or laparoscopic procedures. Although torque wires are disclosed here, any suitable material may be used that would convey the applied rotation from one end of the arm 30 to the other. Preferably, the arms 30 and torque transmission members 32 may be made of stainless steel or any other suitable material that may be used in internal medical procedures.

In certain embodiments, such as in FIG. 2, the arms 30 may comprise a plurality of torque transmission members 32, 34. For instance, a first torque transmission member 32 may be hollow and defines a lumen extending through the length of the first torque transmission member 32. This hollow lumen may be of a sufficient diameter to permit the passage of other material therethrough, such as an inner diameter of 0.005 inch for example. For instance, in some embodiments, a second torque transmission member 34 may be disposed coaxially within the hollow lumen of the first torque transmission member 32. The second torque transmission member 34 therefore may have a smaller diameter than the inner diameter of the hollow lumen of the first torque transmission member 32 noted above. In such embodiments, the first torque transmission member 32 may be rotated by a clinician or user to turn the arm 30, and the second torque transmission member 34 may be rotated separately and independently from the first torque transmission member 32 to rotate or spin an engagement member 40, discussed in greater detail below. In other embodiments, the hollow lumen of the first torque transmission member 32 may be used as a conduit for fluid or materials, such as to supply irrigation to the target site at the working end 3 of the endoscope 2 from an exterior irrigation source or to provide aspiration of fluids and/or materials such as irrigant, blood and tissue from the target site at the working end 3 of the endoscope 2. In certain embodiments, the hollow lumen of the first torque transmission member 32 may be used for both irrigation and aspiration.

As seen in FIGS. 1A-7, each arm 30 includes an engagement member 40 at its distal terminal end. Accordingly, the device 10 may include at least one, but preferably two or more engagement members 40. Each engagement member 40 may be integrally formed with the respective arm 30, such as in FIGS. 6A-7. In other embodiments, the engagement member 40 may be attached to the terminal end of the arm 30. In some embodiments as in FIGS. 1A-C and 5A-5D, the engagement member 40 may be securely attached to the terminal end of the arm 30 such that the engagement member 40 moves together with the movement of the arm 30. In other embodiments, as in FIGS. 2-4B, the engagement member 40 may be movably attached to the arm 30 so that the engagement member 40 may move together with the arm 30 but may also move independently from and relative to the attached arm 30. For example, the engagement member 40 may rotate with rotational motion 7 relative to the axis of the forearm 37 of the attached arm 30 as in FIG. 2. The rotational motion 7 of the engagement member 40 relative to the attached arm 30 may occur from a second torque transmission member 34 disposed coaxially within a first torque transmission member 32, wherein the first torque transmission member 32 provides motion to the arm 30 overall. Further, as depicted in FIG. 2, each engagement member 40 may rotate in either a clockwise or counterclockwise direction depending on the direction of torque or rotation supplied by the second torque transmission member 34, and the various engagement members 40 may rotate in the same or different directions compared to one another. The various engagement members 40 may rotate simultaneously or separately.

Each engagement member 40 includes at least one surface configured to contact the target tissue 9 located distally from the working end 3 of the endoscope 2 and to facilitate engagement of the target tissue 9. As used herein, "engage" or "engagement" of tissue includes, but is not limited to, encountering, contacting, gripping, pinching, holding, retaining, restraining, grasping, hooking, adhering and any other method of locating and/or retaining the device 10 at a particular location along the tissue, such as in the GI tract. The contact surface of the engagement members 40 may include any suitable geometry, such as planar, curved, angular, and may have any number and form of extension or depression to create frictional areas such as ribbing or dimpling for increased contacting/gripping capability. For instance, as seen in FIGS. 1A-1C, the engagement members 40a may include frictional elements such as extensions or ribbing on at least one contact surface to increase engagement with the target tissue 9 for better gripping. In other embodiments, the engagement members 40b may be tubular in shape and have a rounded terminal end as in FIG. 6A-6C. In some embodiments, such as in FIG. 7, the engagement members 40c may include a lumen extending therethrough and an opening where the lumen terminates. The engagement member 40c lumen may be in fluid communication with the hollow lumen of a first torque transmission member 32 or arm 30 and may provide irrigation or aspiration therethrough. In other embodiments, as in FIGS. 2-4B, the engagement members 40d may be formed of an irregular shape such as a gear. The gear may be tooth-shaped, saw-shaped or otherwise, and may have any number of teeth or extensions (such as 2-20 teeth) which may extend from the circumferential surface of the engagement member 40d by any distance. The teeth may be sharp, blunted or rounded at the outermost edges. In some embodiments, the gear may have a diameter in the range of 0.002-0.30 inches measuring from the center of the gear to the most radially outward point, and may have a thickness in the range of 0.01-0.03 inches. In still other embodiments, as in FIGS. 5A-5D, the engagement members 40e may have a substantially planar configuration and the contact surface may be planar. These are but a few illustrative examples and are not intended to be an exhaustive list. The engagement members 40 may be made of any material that is appropriate for use in internal medical procedures and has sufficient rigidity to withstand applied force and grip tissue 9. Examples include but are not limited to nitinol, stainless steel, silicone, silicone rubber, plastic, and titanium.

Each arm 30 and corresponding engagement member 40 is collectively configured to be movable together. For instance, rotational motion 7 of the arm 30 may result in the movement of the corresponding engagement member 40 along a curved pathway, as shown in FIG. 1A. Because the bend 36 breaks the plane of the arm 30, the engagement member 40 at the terminal end of the arm 30 is not coaxial with its corresponding arm 30. Further, despite the arm 30 being sufficiently flexible to traverse a tortuous path, the bend 36 and/or forearm 37 have sufficient rigidity to direct and hold the engagement member 40 out of the axis of the arm 30. In at least one embodiment, the bend 36, forearm 37 and engagement member 40 are fixed relative to one another so that rotational motion 7 of the arm 30 results in a sweeping motion along a curved pathway in the lateral direction 8 that is perpendicular to the longitudinal axis of the arm 30. As used herein, "lateral" refers to a direction that is perpendicular to the longitudinal direction, and may be linear or arcuate.

The engagement members 40 are movable between at least a first position and a second position. In the first (open) position, shown in FIG. 1A, engagement members 40 are spaced apart from one another by a first distance that is sufficiently large that at least one engagement member 40 is not contacting the target tissue 9 and the engagement members 40 do not touch one another. In the second (closed) position, as shown in FIGS. 1B and 1C, the engagement members 40 are spaced apart a second distance from one another that is smaller than the first distance, so the engagement members 40 are closer to one another than in the first position. The engagement members 40 may still not contact one another in the second position, but at least one or both may engage tissue 9 in the second position. The second distance is therefore small enough that tissue 9 may be gripping and held between adjacent engagement members 40 in the second closed position. Although two positions are described here, the engagement members 40 may be movable to any number of positions, such as along a continuum or various discrete positions, and which may be between the first and second positions or beyond the first and second positions.

The engagement members 40 are movable by movement of the attached arms 30. Because the bend 36 and forearm 37 of the arms 30 are sufficiently rigid to convey motion to the connected engagement member 40, the engagement member 40 moves together with at least the bend 36 and forearm 37. Further, because each arm 30 is movable independently of the other arm(s) 30, each engagement member 40 is similarly movable independently of the other engagement member(s) 40.

The arms 30 may be moved in a number of ways to move the engagement members 40. For instance, in at least one embodiment as shown in FIG. 1A, the arms 30 may be moved by rotational motion 7 relative to the body 20 which results in the corresponding engagement members 40 moving in a similar lateral direction 8. Opposing rotational motion 7 applied to different arms 30, such as clockwise motion applied to one arm 30 and counterclockwise motion applied to another arm 30, results in the corresponding engagement members 40 moving in opposing lateral directions 8. For example, if one arm 30 of FIG. 1A is rotated clockwise and the other arm 30 is rotated counterclockwise, the engagement members 40 may be moved closer together, as depicted in FIG. 1B. As the engagement members 40 move closer together, the target tissue 9 between them may be gripped between the closing engagement members 40. The more the arms 30 are rotated, the more pressure the engagement members 40 exert on the target tissue 9 and the harder the grip on the tissue 9 becomes. At some point, enough force is applied and the grip on the tissue 9 is strong enough that the device 10 acts as an anchor for the endoscope 2, preventing the tissue 9 from slipping or moving out of position. The point(s) at which gripping and/or anchoring is achieved may depend on the geometry or material of the engagement member 40, or the type or shape of the tissue 9 to be gripped, among other factors. Rotation of the arms 30 in the opposite directions moves the engagement members 40 further away from one another, reducing the pressure the engagement members 40 exert on the tissue 9 and releasing the tissue 9 from the grip.

In other embodiments, as shown in FIG. 1C, translational motion 6 may be applied to the arms 30 to move them, as well as the corresponding engagement members 40, relative to one another in a longitudinal direction. As used herein, "translational" and "longitudinal" may be used interchangeably to refer to an axial direction of the length of the endoscope 2 extending between the distal working end 3 and the proximal end located outside the patient during a procedure. Accordingly, the engagement members 40 may be moved in a longitudinal direction between a first (open) position (not shown) and a second (closed) position, shown in FIG. 1C. As before, moving the arms 30 in opposing directions relative to the body, and one another, may bring the engagement members 40 closer together or further apart, depending on the opposing directions moved. For instance, when the distal-most extending arm 30 is moved proximally and the more proximally-extending arm 30 is moved distally, the space separating the respective engagement members 40 decreases, resulting in a closer position between the engagement members 40 and increased gripping force. The reverse is also true, such that moving the distal-most extending arm 30 further distally and the more proximally-extending arm 30 further proximally increases the space between the respective engagement members 40 and reduces the gripping force. Further, in some embodiments, the contact surface of the engagement members 40 when moved in the longitudinal direction may be a different surface from the contact surface when moved in the lateral direction. In other embodiments, the contact surface of the engagement members 40 may be the same surface regardless of motion in a lateral or longitudinal direction.

It should also be appreciated that movement of the arms 30 to achieve the desired positioning of the engagement members 40 may include a combination of translational motion 6 and rotational motion 7 of the arms 30. For instance, the arms 30 may first be rotated to bring the engagement members 40 closer together in the lateral direction, and then the arms may be moved axially by translational motion to bring the engagement members 40 closer together in the longitudinal direction. Further, at least one arm 30 may be moved to facilitate motion of the engagement members 40 between positions such as a first (open) and second (closed) position, while another arm 30 remains stationary. In other embodiments, both arms 30 may be moved relative to one another. Each arm 30 may therefore be moved or held stationary relative to the other arm(s) 30 in any direction and by any amount, degree or distance to move the engagement members 40 between various positions for gripping, anchoring and release of tissue 9.

The body 20 of the device 10 may further include at least one recess 28 which is dimensioned to receive at least a portion of an engagement member 40. As shown in FIGS. 4A-7, the recess 28 may be configured to have similar dimensions as the engagement members 40. The recess 28 may preferably be larger in size than the engagement members 40 to receive the engagement members 40 therein. In some embodiments however, the recess 28 may be smaller than the entire engagement member 40 but may be sufficiently dimensioned to receive at least a portion of the engagement member 40. For instance, in FIGS. 3A-3B, each engagement member 40d may include a biasing element 42, such as a spring arm or other resiliently deformable mechanism. The recess 28 may be dimensioned to receive the biasing element 42 of the engagement member 40d, rather than the entire engagement member 40d itself.

In at least one embodiment, such as shown in FIGS. 4A-5D, the recess 28 is sized and dimensioned to receive the entire engagement member 40 therein. There may be a single recess 28 that receives both or all engagement members 40, or there may be multiple recesses 28 each dimensioned to receive a corresponding engagement member 40.

The engagement members 40 may be moved into and out of the recess(es) 28 for stowing during placement or retraction of the endoscope 2 and attached device 10. While extending the engagement members 40 from the working end 3 of an endoscope 2 during a procedure is helpful to a practitioner in being able to manipulate the tissue 9 and hold it out of the way so the procedure can occur unimpeded, the presence of the engagement members 40 in such a position during ingress and egress from the procedure site may be problematic. The engagement members 40 may unintentionally snag on surrounding tissue or organs along the way while traversing the many turns and bends of the GI tract, for instance, and can cause unintended ripping or tearing of healthy tissue.

Figure 4A:
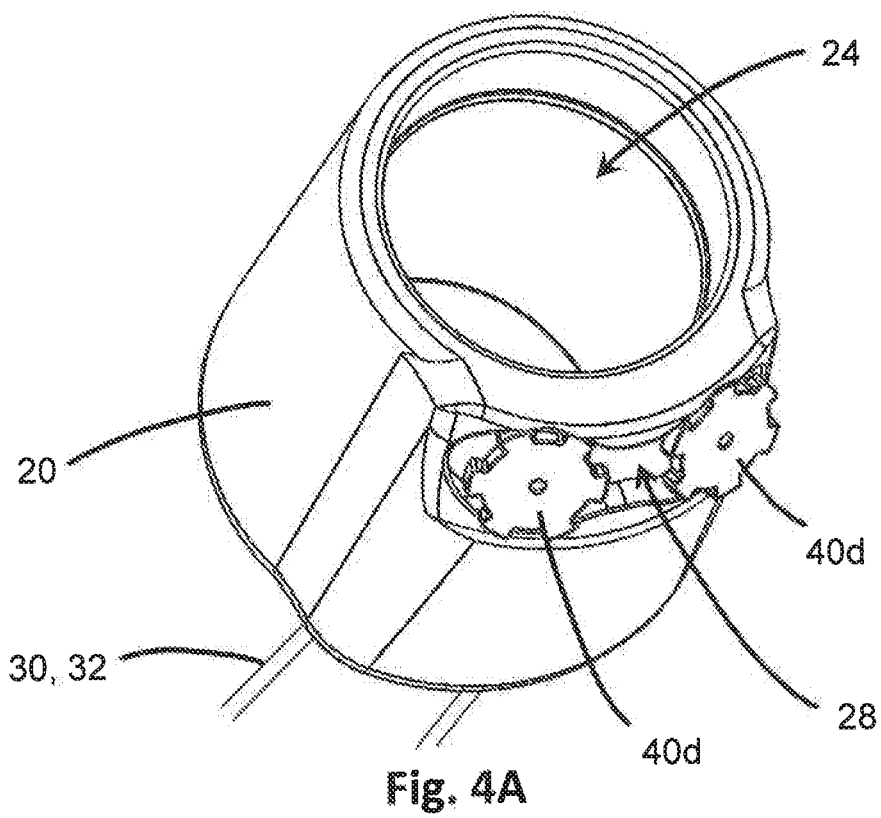
FIG. 4A is an isometric schematic diagram of a fourth embodiment of the distal end of the device, showing gear-shaped engagement members stowed in a recess within the device body.
Figure 4B:
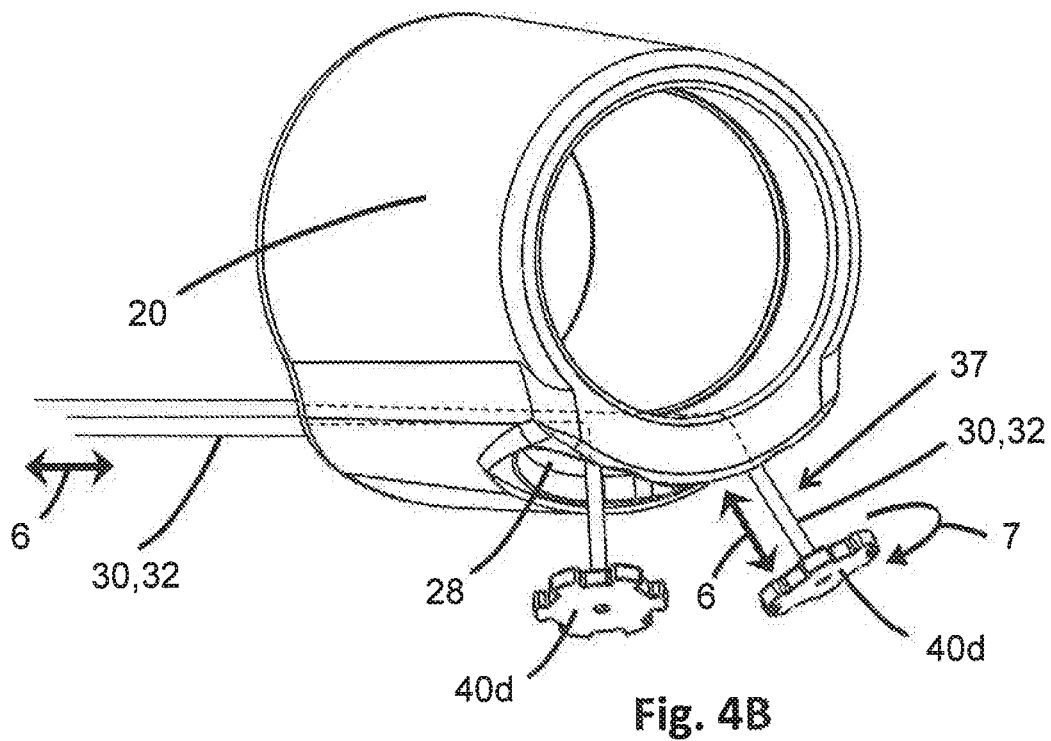
FIG. 4B is an isometric view of the device of FIG. 4A, showing the engagement members extended in an operational position.

Therefore, in at least one embodiment of the present device 10, the engagement members 40 may be movable into and out of a recess 28 in the body 20 of the device 10. As with other movement described above, the engagement members 40 may be moved by controlling the movement of the corresponding arm 30, and may be by any combination of translational motion 6 and rotational motion 7 applied to the arms 30. For instance, as depicted in FIGS. 4A and 4B, the engagement members 40d may be stored in the recess 28 of the body 20 during placement or retraction of the device 10 and endoscope 2. Once the desired target site is reached, the engagement members 40d may be released from the recess 28 by moving the respective arms 30 with translational motion 6 in the distal direction 14. This longitudinal motion extends the arms 30 through the body 20, resulting in movement of the engagement members 40d outwardly from the recess 28 and the body 20. When the procedure is over and the device 10 and endoscope 2 need to be retracted, the arms 30 may be moved translationally in the proximal direction. As the arms 30 are retracted, the engagement members 40 are pulled into the recess 28 of the body 20 where they are stored during removal of the device 10 and endoscope 2. In some embodiments, as in FIGS. 3A and 3B, when the arms 30 are pulled in, biasing elements 42 are pulled into and stowed in the recess 28. When the arms 30 are pushed out in the distal direction, the biasing elements 42 push the ends of the arms 30, and thus the engagement members 40d, apart from one another.

In still further embodiments, as in FIGS. 5A-5D, the arms 30 may be rotated and translated to move the gripping arms 40 into and out of the recess 28. For instance, each arm 30 may be independently rotated about its axis by rotational motion 7 to move the engagement member 40e away from the tissue 9 and/or the other engagement member(s) 40. Rotational motion 7 may also be used to maneuver the engagement member 40 into alignment with the corresponding recess 28 or portion of recess 28 that is dimensioned to receive that engagement member 40. For instance, recess 28 or portion of recess 28 receiving the engagement member 40 may be configured to correspond to a particular geometry of the engagement member 40, which may be specific to a particular orientation of the engagement member 40. Rotational motion 7 may be used to position the engagement member 40 in the proper orientation to align with the shaped recess 28. In other embodiments, however, the recess 28 may not be correspondingly shaped or configured to the engagement member 40, but may simply have a large enough dimension to receive the engagement member 40 therein regardless of its orientation.

Figure 5A:
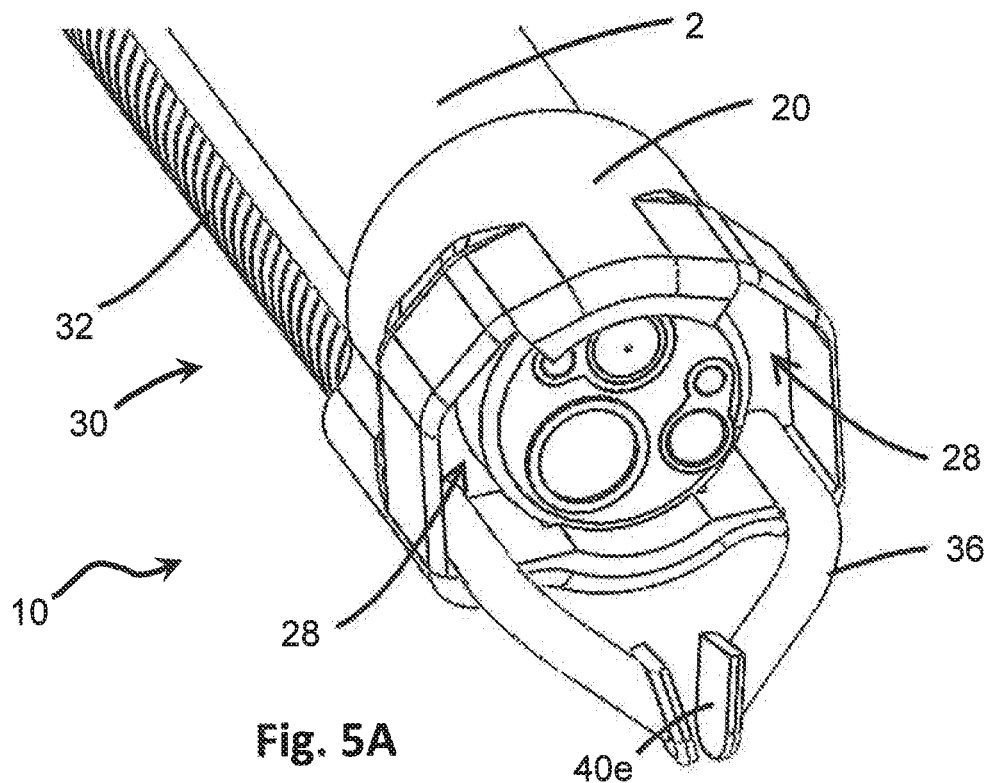
FIG. 5A is an isometric schematic diagram of a fifth embodiment of the distal end of the device in connection with the distal end of an endoscope, where the engagement members have a planar configuration.
Figure 5B:
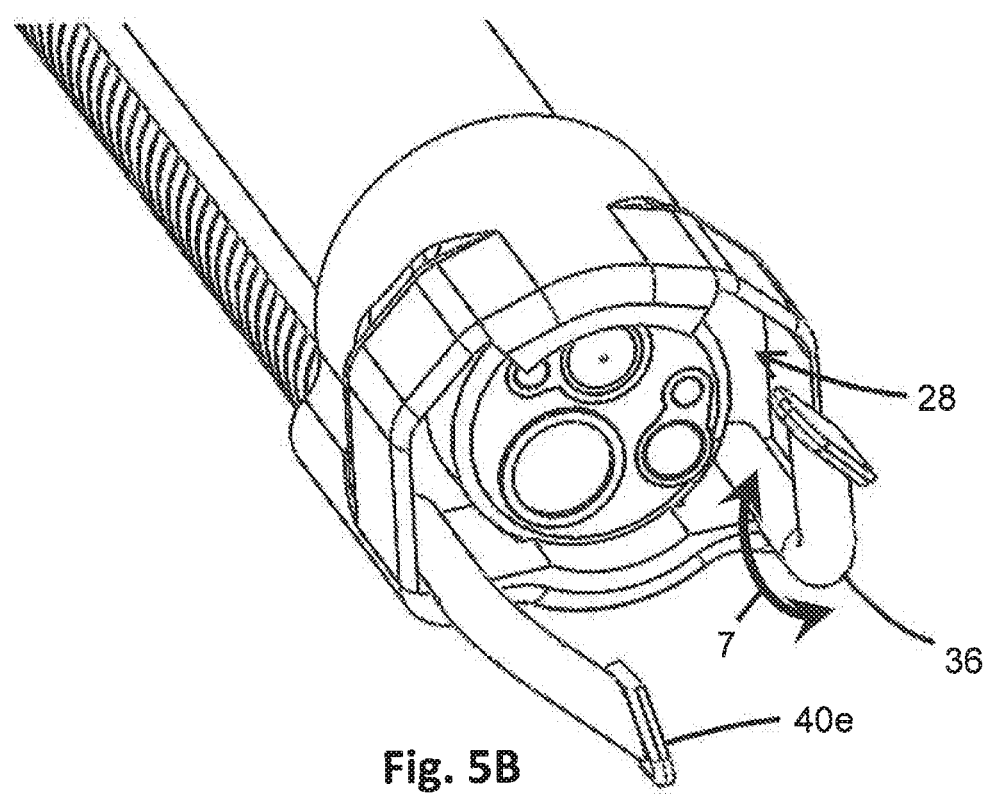
FIG. 5B is an isometric view of the device of FIG. 5A, showing one engagement member rotated in preparation for stowing in a recess within the device body.
Figure 5C:
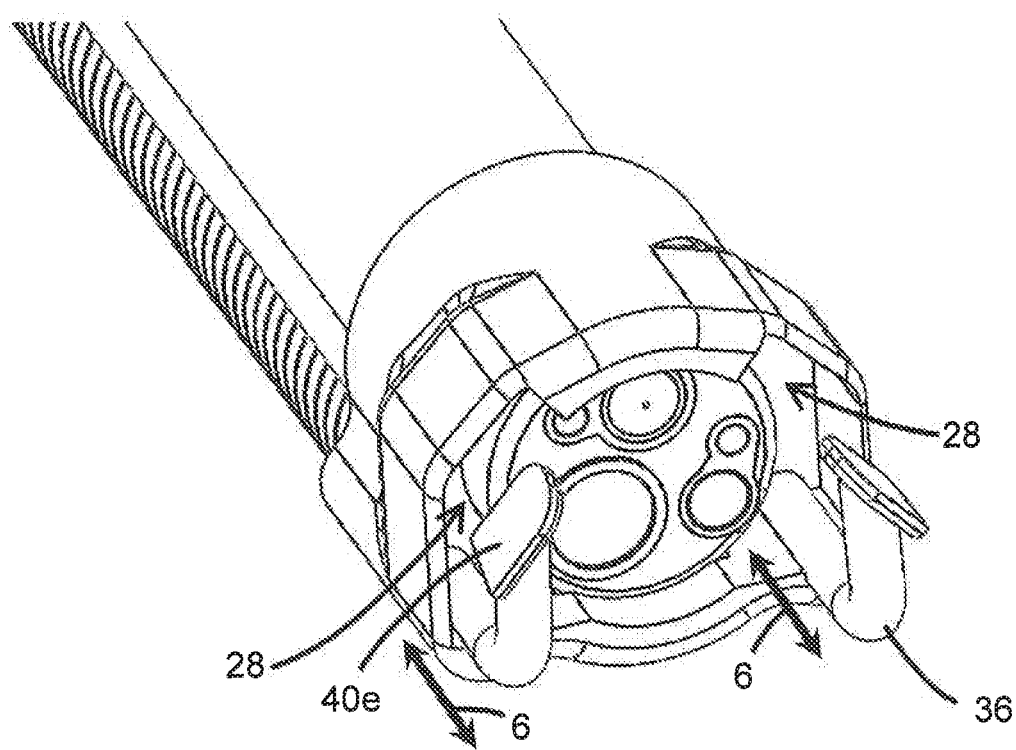
FIG. 5C is an isometric view of the device of FIG. 5A, showing both engagement members rotated in preparation for stowing in a recess within the device body.
Figure 5D:
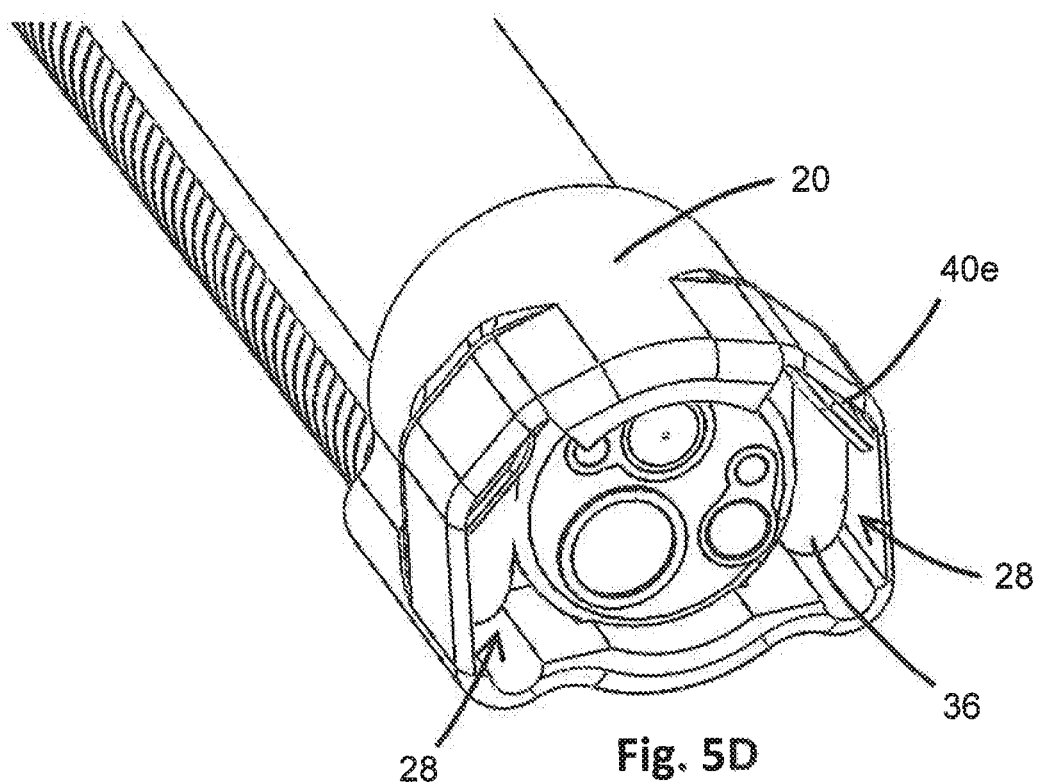
FIG. 5D is an isometric view of the device of FIG. 5A, showing both engagement members stored in a recess within the device body.

Once the engagement member 40 is properly oriented with respect to the recess 28, translational motion 6 in a proximal direction may be applied to the arm 30 to move the engagement member 40 into the recess 28, as shown in FIG. 5C. When fully stowed, the engagement member 40 may be entirely retained within the recess 28, as in FIG. 5D. In other embodiments, as in FIGS. 6A-6C, the recess 28 may be open-ended. Here, the engagement members 40b are fully received within the recess 28, but they are not entirely encompassed within the body 20. However, even in such embodiments, the engagement members 40b do not extend beyond the terminal distal end of the body 20, shown in FIG. 6C, thus minimizing the possibility of being inadvertently dragged or caught along tissue during deployment or retraction of the endoscope 2 through the GI tract.

Figure 8:
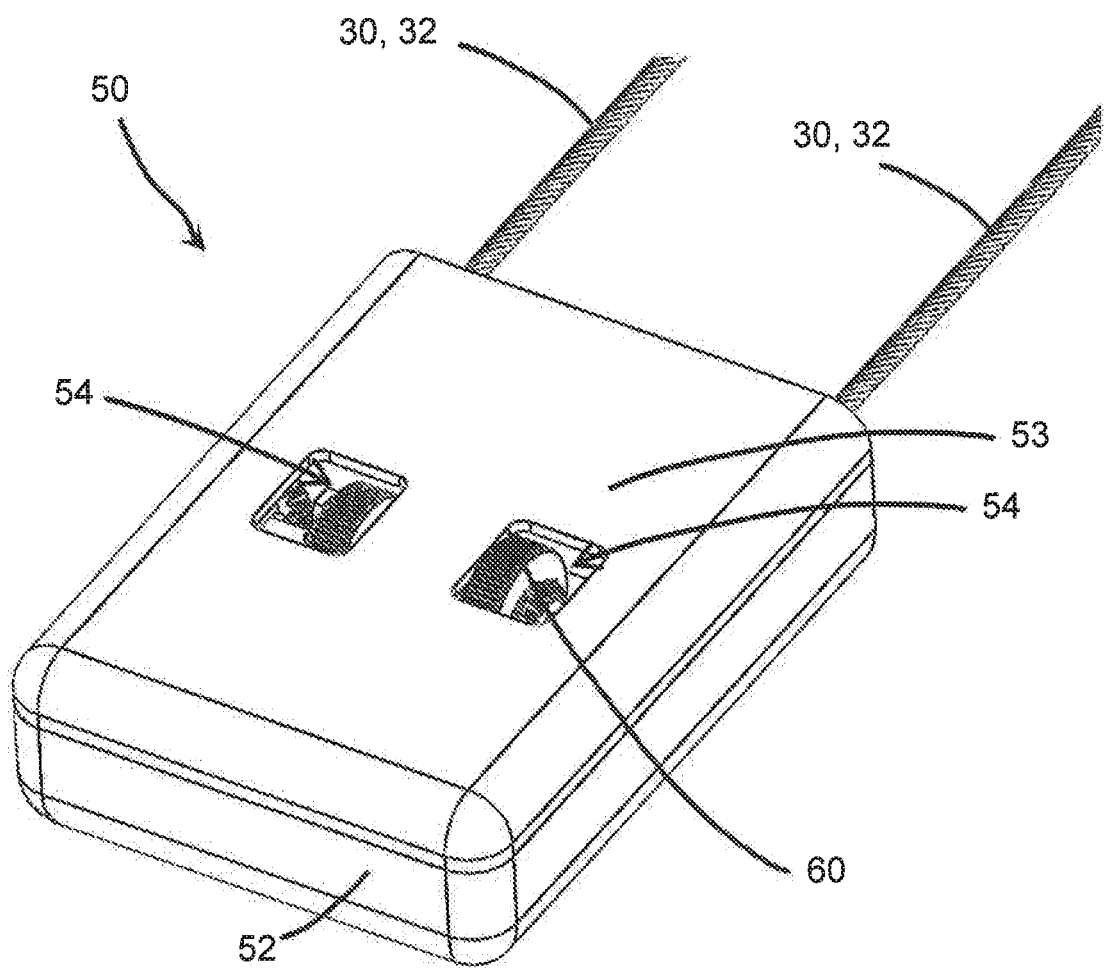
FIG. 8 an isometric schematic diagram of one embodiment of the handpiece of the device.
Figure 9:
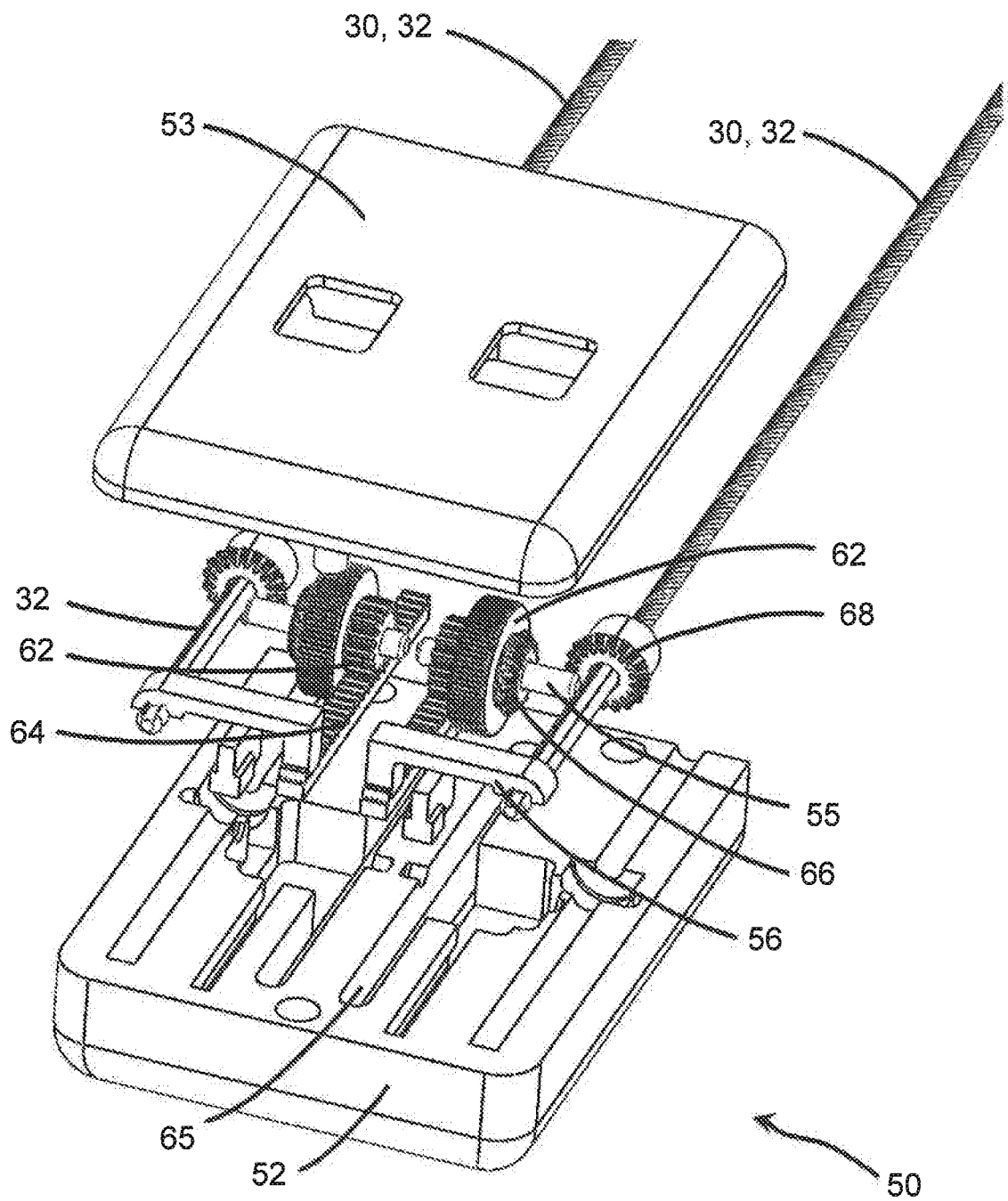
FIG. 9 is an exploded view of the handpiece of FIG. 8.

As shown in FIGS. 8-15, the device 10 also includes a handpiece 50 at the proximal end that remains outside of the patient during a medical procedure. The handpiece 50 is operated by the clinician or user to control the arms 30 and engagement members 40 at the distal end of the device 10. In some embodiments, the handpiece 50 may be handheld or placed on a table or other flat surface, such as in FIG. 8. In other embodiments, as in FIGS. 12 and 13, the handpiece 50' may be attachable to the medical instrument or endoscope 2 by an attachment mechanism 51, such as but not limited to a clip, that connects by snap fit, push fit, or connection members such as screws, pins, or other attachment method. The handpiece 50 may include a handpiece base 52 and handpiece cover 53 that collectively form a housing that retains the various other components of the handpiece 50, such as shown in FIGS. 8 and 9. The handpiece base 52 and handpiece cover 53 may be removably secured to one another, such as by snap fit, push fit, screws, pins, etc.

The proximal ends of the arms 30 terminate at or in the handpiece 50. Accordingly, the handpiece 50 is configured to receive a portion of the arms 30. The handpiece 50 further includes mechanisms by which a clinician or operator may control the arms 30. For instance, the handpiece 50 includes at least one actuator 60 that is connected to at least one of the arms 30 and drives the motion of the arm(s) 30. Preferably, each arm 30 may have a dedicated actuator 60 so the arms 30 may be easily controlled independently of one another. In certain embodiments, however, a single actuator 60 may be connected to multiple arms 30 and can selectively control the various arms 30 independently though interconnected. While preferably mechanically connected, in certain embodiments the actuator 60 may be electronically connected to the arm(s) 30 and may control the motion of the arm(s) 30 electronically, such as through a computer program that may operate servos configured to translational and/or rotational motion. In at least one embodiment, however, the actuator 60 is a thumb wheel as shown in FIGS. 8-15 that can be operated by a thumb or finger of the user, and each actuator 60 connects to a different arm 30. The handpiece 50, 50' may also include at least one aperture 54 extending through a wall, such as the handpiece cover 53. Each aperture 54 may be dimensioned to receive and permit movement of an actuator 60 therein. Accordingly, the actuator(s) 60 may be located partially within and partially outside of the handpiece 50, 50' so a clinician or user may engage the actuator(s) 60 from the outside of the handpiece 50, 50'.

FIGS. 9-15 illustrate various ways in which each actuator 60 may control the rotational and translational motion 6, 7 of an arm 30. Each actuator 60 is rotatably and slidingly disposed about an axle 55, and may be a thumbwheel as shown. The axle 55 may be fixed to the handpiece 50 or may be floating and freely rotate with the actuator 60 within the handpiece 50. The actuator 60 may be activated by turning or rotating the actuator 60 about the axle 55. Depending on the location of the actuator 60 along the axle 55, the actuator 60 may drive either translational or rotational motion of an arm 30.

Figure 10:
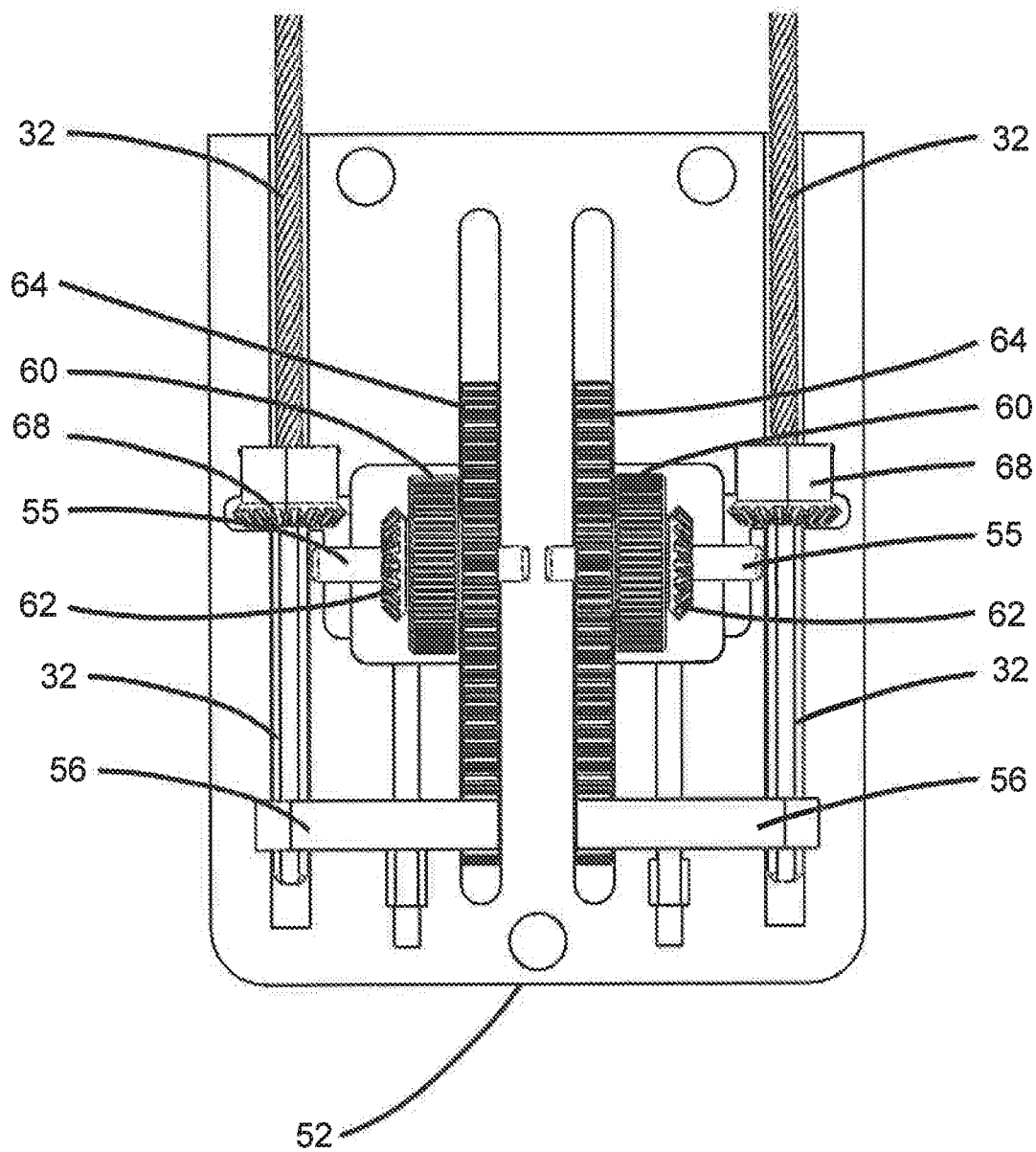
FIG. 10 is a top plan view of the inside of the handpiece of FIG. 8.
Figure 11A:
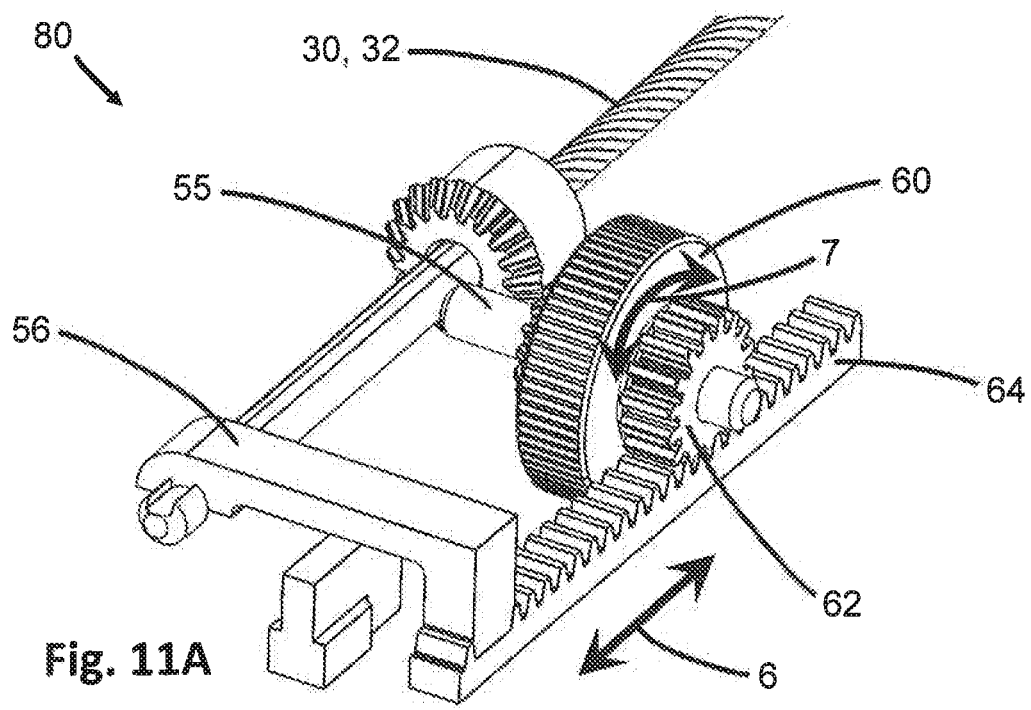
FIG. 11A is an isometric view of one gear assembly of the handpiece of FIG. 8, showing the translational gear and track engaged to provide translational motion to the arm.
Figure 11B:
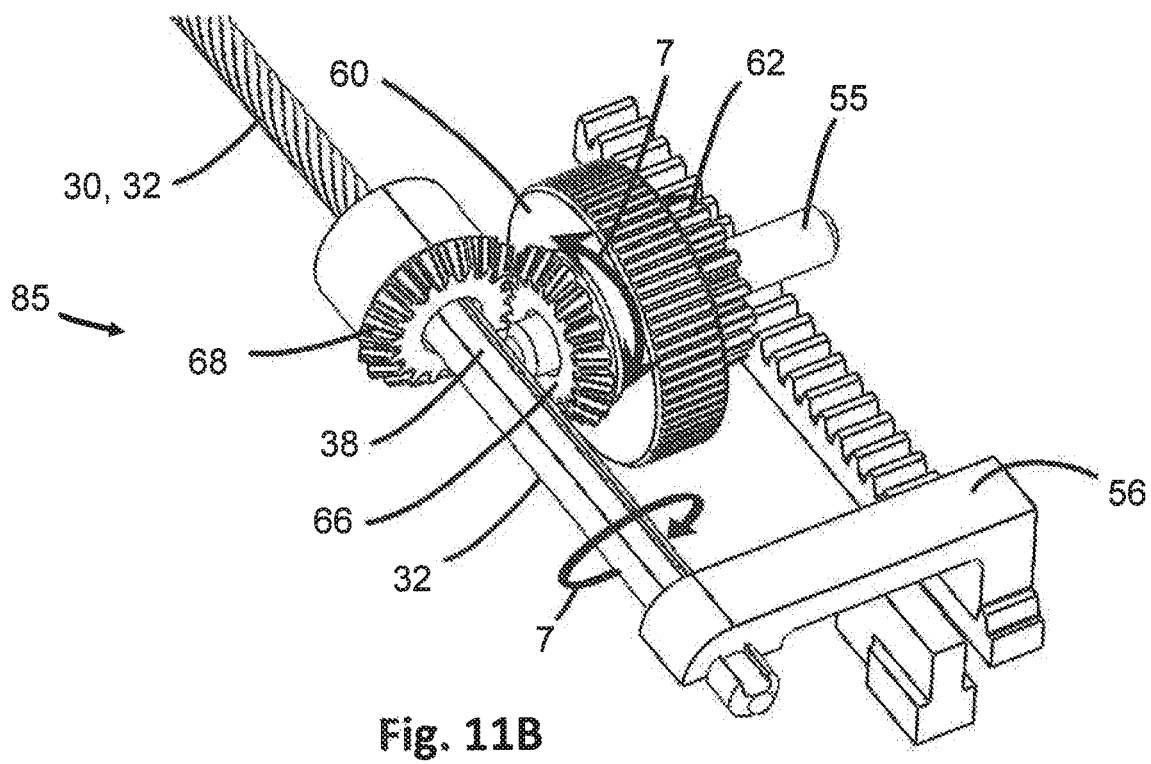
FIG. 11B is an isometric view of the gear assembly of FIG. 11A, showing first and second rotational gears engaged to provide rotational motion to the arm.

The handpiece 50 further includes at least one of a translational adjustment mechanism 80 and a rotational adjustment mechanism 85. The translational adjustment mechanism 80 is configured to selectively provide translational motion 6 to the arm 30. In at least one embodiment as shown in FIGS. 9-11A, the translational adjustment mechanism 80 may include a translational gear 62 fixedly secured to the actuator 60. The translational gear 62 may be a pinion having teeth extending outwardly from the circumference. In other embodiments, the actuator 60 itself may include teeth or other features extending from one side thereof in place of the translational gear 62. The translational adjustment mechanism 80 may also include a translational track 64 extending in the longitudinal direction parallel to the arms 30, as shown in FIG. 10. The translational track 64 may be a rack, also having teeth extending from a surface thereof. In a preferred embodiment, the handpiece 50 further includes a groove 65 dimensioned to slidably retain the translational track 64. Accordingly, the groove 65 may be longer than translational track 64 and may limit the range of motion of the translational track 64. The translational gear 62 and translational track 64 are dimensioned and configured so their respective teeth interlock and transfer motion as one is moved relative to the other. For instance, when the actuator 60 is positioned along the axle 55 so the translational gear 62 engages the translational track 64, and the actuator 60 is rotated about the axle 55 such as by turning with a thumb or finger, the rotation of the actuator 60 drives the rotation of the translational gear 62 fixedly attached thereto. As the translational gear 62 rotates, its teeth interlock with and apply force to the teeth of the translational track 64, moving the translational track 64, shown in FIG. 11A. The direction of movement of the translational track 64 depends on the direction of rotation of the translational gear 62, and thus the direction of rotation of the actuator 60. The translational track 64 may move through the groove 65 until it is stopped in one direction or another by the end of the groove 65 or cessation of the translational gear 62 motion. A rigid bridge 56 connects to the translational track 64 at one end and to the arm 30 at the other end, shown in FIGS. 9 and 10. As the translational track 64 is moved in a longitudinal direction, the bridge 56 transfers this motion to the arm 30, thus causing the arm 30 to similarly move in the longitudinal direction. Accordingly, the arm 30 is moved by translational motion 6 in a longitudinal direction either distally toward the working end 3 of the endoscope 2 or proximally toward the handpiece 50. When translational motion 6 is no longer desired, rotation of the actuator 60 may be stopped and the user may slide the actuator 60 along the axle 55 to disengage the translational gear 62 from the translational track 64.

The handpiece 50 also includes a rotational adjustment mechanism 85 interconnecting the actuator 60 and arm 30, and is configured to provide rotational motion 7 to an arm 30 upon engaging the actuator 60. In at least one embodiment, as in FIGS. 9-10 and 11B, the rotational adjustment mechanism 85 may include a first rotational gear 66 fixedly secured to the opposite side of the actuator 60 from the translational gear 62. The first rotational gear 66 may be any type of rotational gear having teeth, such as but not limited to a bevel, miter, gear or pinion. The rotational adjustment mechanism 85 may further include a second rotational gear 68 at least partially circumferentially secured around a portion of the arm 30 located within the handpiece 50. The second rotational gear 68 may also be any type of rotational gear, such as a bevel gear or pinion, and may be the same or different type of gear as the first rotational gear 66. The second rotational gear 68 may be secured to the outer circumference of the arm 30, such as by crimping, welding, adhesive, or other securing mechanism, or may be otherwise connected such that movement of the second rotational gear 68 is conveyed to the arm 30. Accordingly, the actuator 60 may be slidably moved along the axle 55 in the direction of the rotational gears 66, 68 until the teeth of the first rotational gear 66 and second rotational gear 68 interlock. In this position, as the actuator 60 is rotated, the first rotational gear 66 also rotates. The teeth of the first rotational gear 66 apply pressure on the engaged teeth of the second rotational gear 68 until the second rotational gear 68 begins to turn. The second rotational gear 68 may include an internal extension member (not shown) that is received within a keyway 38 along the arm 30, shown in FIG. 11B. The internal extension member applies force to the keyway 38 as the second rotational gear 68 is rotated until the arm 30 through which the keyway 38 extends begins to rotate. In this manner, the rotation of the actuator 60 results in rotational motion 7 of the arm 30.

In at least one embodiment, actuator 60 is movable along the axle 55 to a first or second position to selectively engage either the translational adjustment mechanism 80 or the rotational adjustment mechanism 85. Rotational and translational motion may therefore be applied to the arm 30 independently of one another. In some embodiments, however, the axle 55 may be of a small enough length that both the translational gear 62 and first rotational gear 66 simultaneously engage the translational track 64 and second rotational gear 68, respectively. In such embodiments, both translational and rotational motion may be achieved at the same time, although the directions may be coupled. For instance, translational motion 6 may occur in a distal direction and counterclockwise rotational motion 7 may necessarily also occur from rotation of the actuator 60 in one direction, depending on the configuration of the actuator 60, translational gear 62 and first rotational gear 66. This is just an illustrative example, and any combination of translational motion direction and rotational motion direction is possible depending on the various configurations of the actuator 60, translational gear 62 and first rotational gear 66. Also, control of one arm 30 has been described above in relation to one actuator 60. It should be appreciated that each actuator 60 may control each associated arm 30 in a like manner, although each may be operated independently of the other for selective and independent control.

Figure 14:
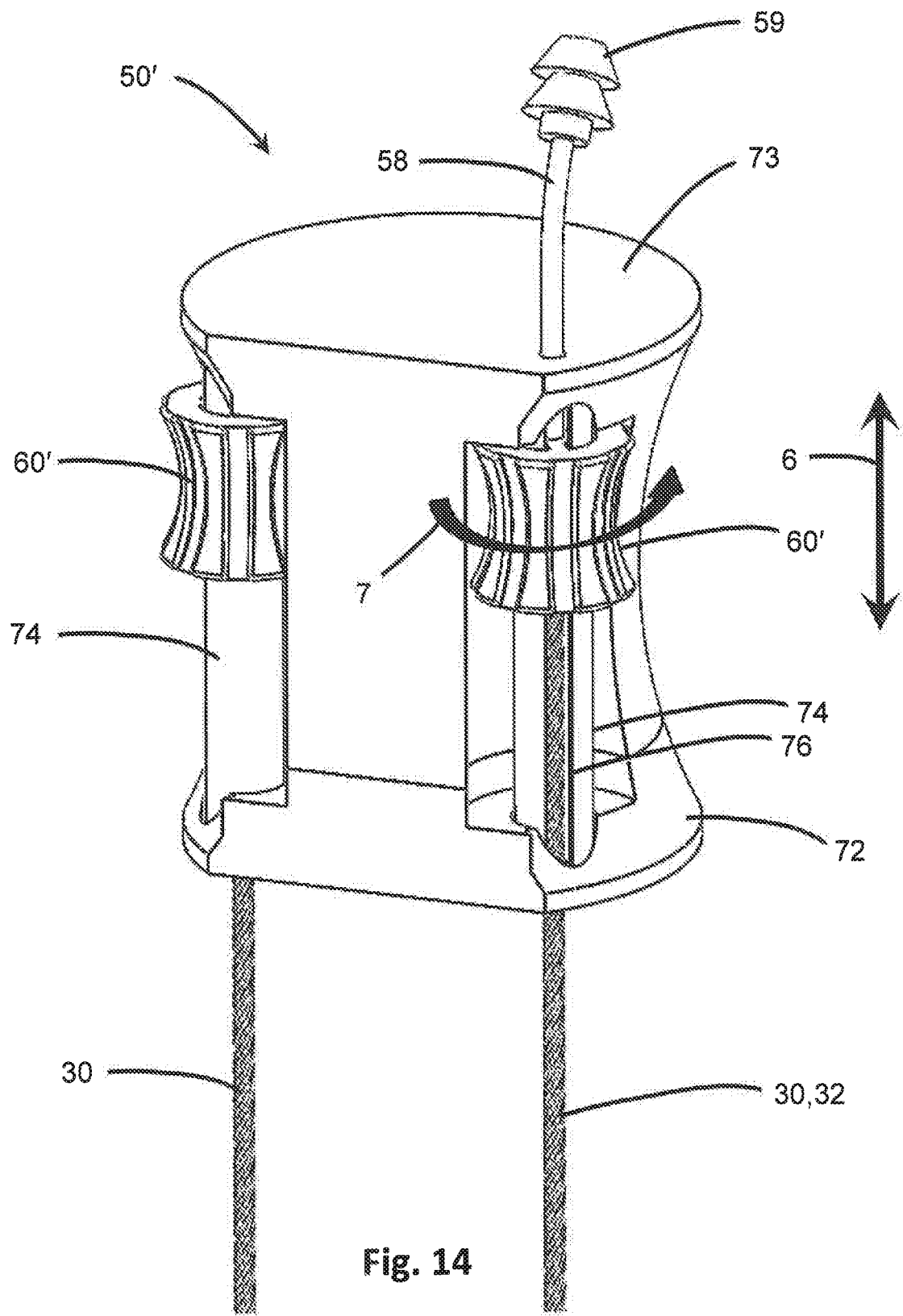
FIG. 14 is a partial cross-sectional view of the handpiece of FIG. 12, showing a cross-section of the slider.
Figure 15:
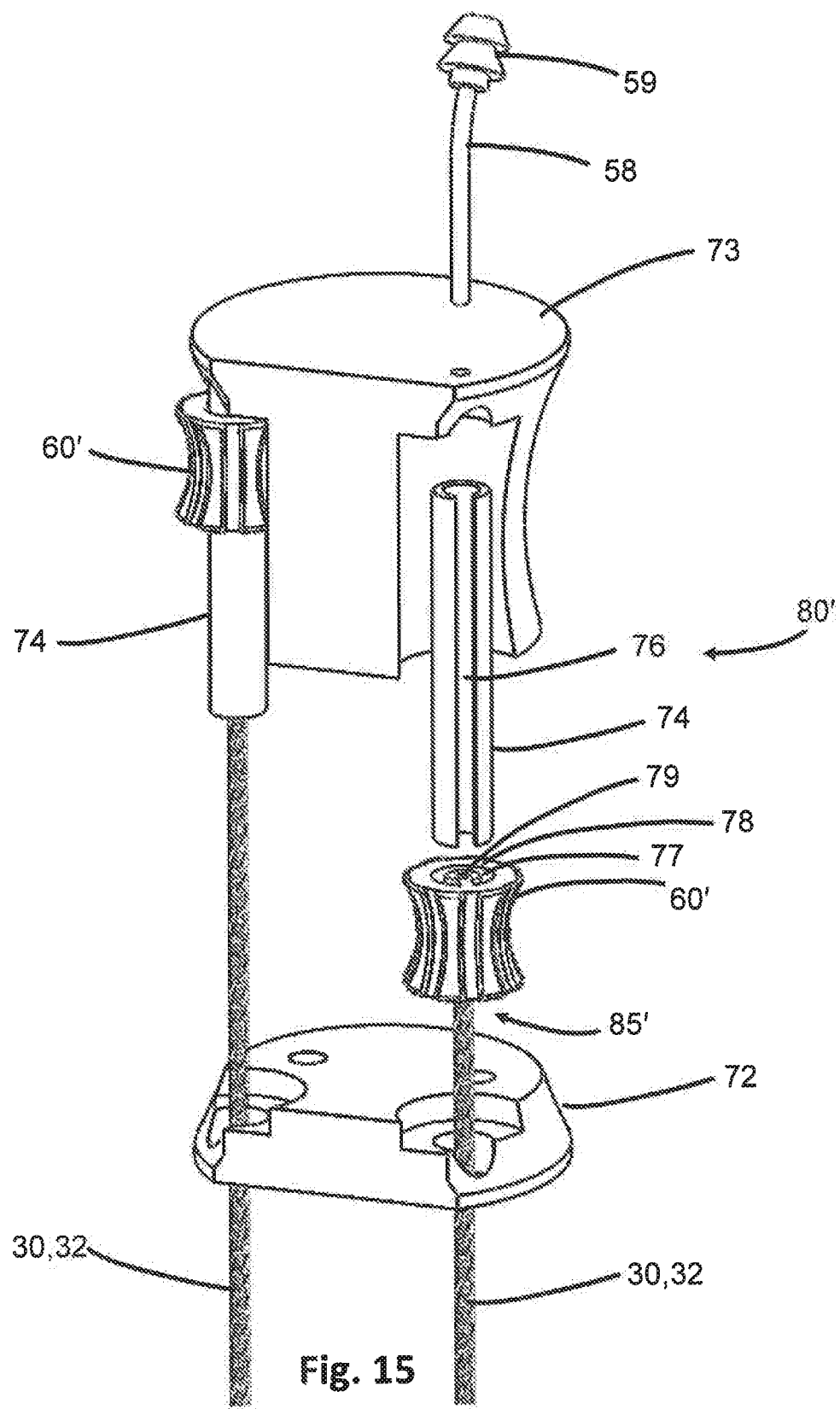
FIG. 15 is an exploded view of the handpiece of FIG. 12.

In at least one other embodiment, as in FIGS. 14-15, the rotational adjustment mechanism 85' may include at least one arm 30 bonded or otherwise permanently secured to the actuator 60', such as at the terminal proximal end of the arm 30. Accordingly, application of force to the actuator 60' to rotate the actuator 60' likewise causes the bound arm 30 to also rotate in the same direction. Clockwise rotation of the actuator 60' therefore may cause clockwise motion of the attached arm 30, and counterclockwise motion of the actuator 60' may cause counterclockwise motion of the attached arm 30.

In the embodiment of FIGS. 14-15, the translational adjustment mechanism 80' may include a slider 74 having an elongate length that is disposed longitudinally within the handpiece 50'. The actuator 60' may be movably connected to the slider 74 such that the slider 74 forms a guide for selective movement of the actuator 60' there along in a longitudinal direction. The arm 30 bonded to the actuator 60' also forms part of the translational adjustment mechanism 80', conveying the translational motion 6 of the actuator 60' along the slider 74 to the attached arm 30, so the arm 30 similarly moves with the same translational motion 6. The distance of possible translational motion 6 is limited by the length of the slider 74, which may also be limited by the length of the handpiece 50'.

In some embodiments, as shown in FIG. 15, the actuator 60' may include an actuator channel 78 extending through the actuator 60', such as longitudinally through the actuator 60'. The actuator channel 78 may be correspondingly configured to the shape and dimensions of the slider 74 such that the actuator channel 78 receives and retains the slider 74 therein. Accordingly, the actuator channel 78 may have a diameter or outer diameter that is larger than the diameter of the slider 74. In some embodiments the slider 74 may be tubular, and the actuator channel 78 may be the corresponding negative of a tubular shape. Because the slider 74 is preferably longer than the actuator 60', the slider 78 may extend entirely through and beyond the edges of the actuator 60'.

In certain embodiments, the actuator 60' may be keyed or otherwise have a polarized configuration. Accordingly, the actuator 60' may include a key 77 which may be any shaped extension. The key 77 may extend from the exterior surface of the actuator 60' or may extend inwardly into the actuator channel 78 as in FIG. 15. The key 77 may therefore also define part of the actuator channel 78 in certain embodiments. Regardless of configuration, the key 77 assists in conveying at least one of the rotational motion 7 or translational motion 6 from the actuator 60' to the attached arm 30. For instance, as the actuator 60' is rotated, the key 77 may push against the slider 74 disposed in the actuator channel 78, thus applying additional torque for rotating the attached arm 30. Also, the correspondingly matched configurations of the key 77 and actuator channel key 77 may assist in guiding the actuator 60' along the slider 74. Indeed, the slider 74 may include a slot 76 extending along at least a portion of the slider 74 length and is configured to receive and slidably retain the key 77 of the actuator 60' therein.

Figures 12, 13:
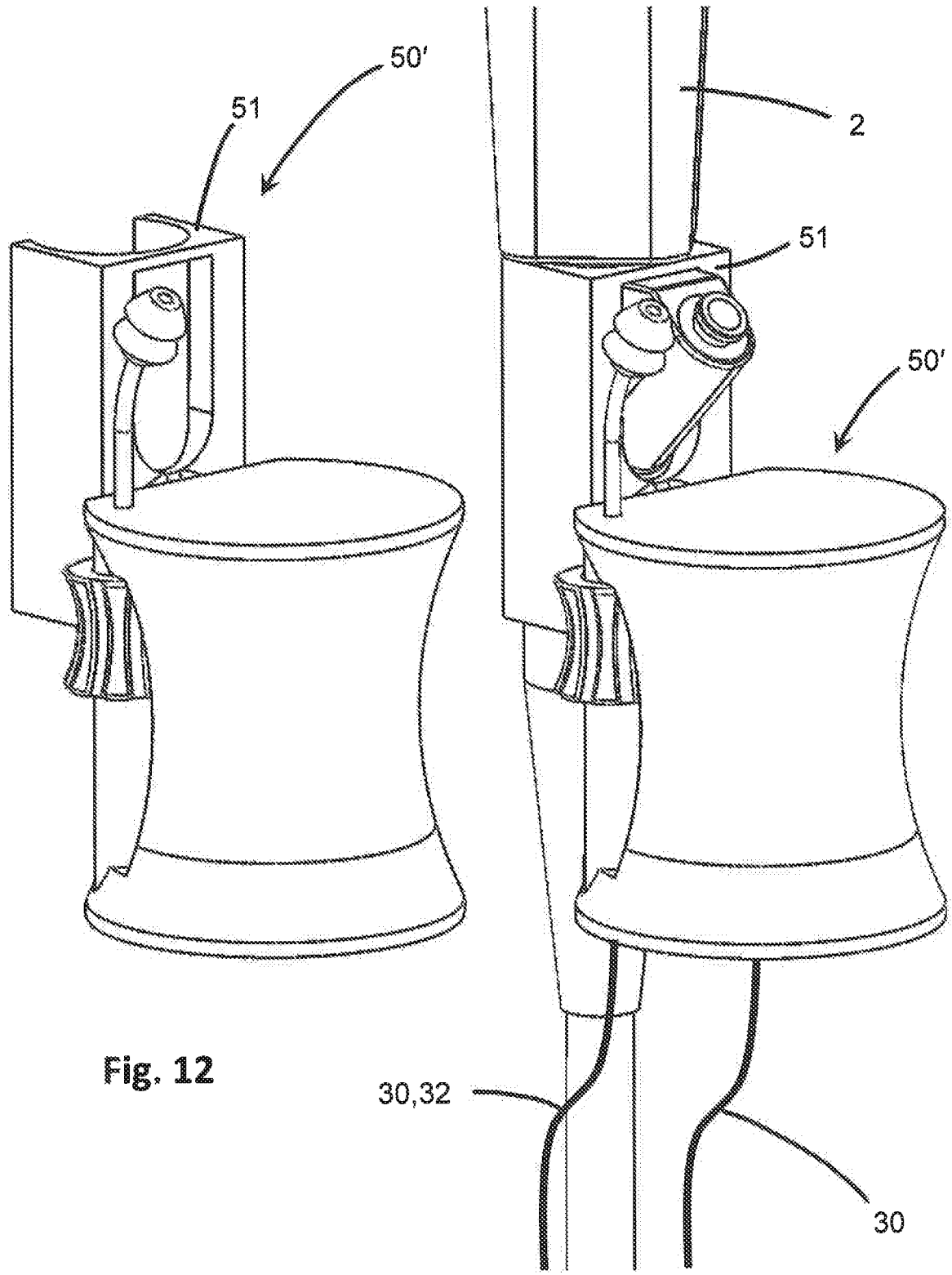
FIG. 12 is an isometric schematic diagram of a second embodiment of the handpiece of the device.
FIG. 13 is an isometric view of the handpiece of FIG. 12 shown in connection with the proximal end of an endoscope.

The actuator 60' may also have an actuator lumen 79 extending therethrough. The actuator lumen 79 may be aligned and in fluid communication with the hollow lumen of the arm 30, such as a hollow first torque transmission member 32 discussed above. The actuator lumen 79 may connect the hollow lumen of the first torque transmission member 32 with a fluid reservoir located outside the device 10, such as to provide irrigation and/or aspiration. The actuator lumen 79 may therefore also connect in fluid communication with tubing 58, which in turn connects to a connector 59 port for accessing the fluid reservoir, as shown in FIGS. 12, 13 and 15. In certain embodiments, the actuator channel 78 may be disposed concentrically around the actuator lumen 79, such as at least partially circumferentially around the actuator lumen 79.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents.

REFERENCE LABELS

2 Medical instrument (endoscope)
3 Working end

4 Face
5 Working channels
6 Translational motion (axial)
7 Rotational motion
8 Lateral direction
9 Tissue
10 Device
12 Distal end (device)
14 Proximal end (device)
20 Body
22 Clip
24 Primary channel
26 Arm channel
28 Recess
30 Arm
32 First torque transmission member
34 Second torque transmission member
36 Elbow
37 Forearm
38 Keyway
40 Engagement member
40a Engagement member (frictional)
40b Engagement member (rounded)
40c Engagement member (rounded with lumen)
40d Engagement member (gears)
40e Engagement member (plates)
42 Biasing element
50 Handpiece (first embodiment)
50' Handpiece (second embodiment)
51 Attachment mechanism
52 Handpiece base
53 Handpiece cover
54 Aperture
55 Axle
56 Bridge
58 Tubing
59 Connector
60 Actuator
60' Actuator (keyed)
62 Translational gear
64 Translational track
65 Groove
66 First rotational gear
68 Second rotational gear
72 Distal end (handpiece)
73 Proximal end (handpiece)
74 Slider
76 Slot
77 Key
78 Actuator channel
79 Actuator lumen
80 Translational adjustment mechanism
80' Translational adjustment mechanism (second embodiment)
85 Rotational adjustment mechanism
85' Rotational adjustment mechanism

What is claimed is:

1. A device for engaging tissue, said device comprising:
a distal end and a proximal end;
a body (i) having a primary channel extending therethrough, said primary channel configured to selectively receive and restrain a distal end of an endoscope, (ii) selectively affixed to and forming said distal end of said endoscope, and (iii) having at least one arm channel extending therethrough receiving at least one arm;
wherein said endoscope has a working end and said body is configured to be completely circumferentially disposed about the working end of the endoscope when said device is attached to the endoscope;
said at least one arm extending from said proximal end to said distal end of said device exterior to the endoscope, said at least one arm selectively movable by at least one of rotational motion and translational motion relative to said body, said at least one arm including at least one engagement member configured to contact and engage tissue;
said at least one engagement member being selectively movable between a first position wherein said at least one engagement member is free from contact with the tissue and a second position wherein said at least one engagement member is in contact with the tissue by at least one of said rotational motion and said translational motion of said at least one arm.

2. The device of claim 1, further comprising a plurality of arms each terminating in one of said engagement members, wherein in said first position, said engagement members are spaced apart by a first distance, and in said second position, said engagement members are spaced apart by a second distance, wherein said second distance is less than said first distance.

3. The device of claim 2, wherein said engagement members are configured to retain the tissue between said engagement members in said second position and to release the tissue in said first position.

4. The device of claim 2, wherein each of said arms is selectively movable independently of the others of said plurality of arms.

5. The device of claim 1, wherein said at least one engagement member includes at least one of a frictional element, rounded configuration, gear shape and planar shape.

6. The device of claim 1, wherein said at least one engagement member includes at least one contact surface configured to engage said tissue in said second position.

7. The device of claim 1, wherein said at least one arm channel extends through said body parallel to said primary channel.

8. The device of claim 1, wherein said at least one arm comprises a hollow lumen.

9. The device of claim 8, wherein said hollow lumen of said at least one arm is in fluid communication with a connector selectively affixable to a fluid source to provide at least one of irrigation and aspiration between said fluid source and said distal end of said body.

10. The device of claim 8, wherein said at least one engagement member further comprises a lumen extending therethrough in fluid communication with said hollow lumen of said at least one arm.

11. The device of claim 1, wherein said at least one arm further comprises a torque transmission member configured to convey torque applied from said proximal end to said distal end.

12. The device of claim 11, wherein said at least one arm further comprises a first torque transmission member that is hollow lumen and a second torque transmission member having a smaller diameter than said hollow lumen of said first torque transmission member, wherein said second torque transmission member is coaxially disposed within said hollow lumen of said first torque transmission member.

13. The device of claim 12, wherein said second torque transmission member is independently and separately movable in relation to said first torque transmission member.

14. The device of claim 12, wherein said at least one engagement member is affixed to said second torque transmission member.

15. The device of claim 1, further comprising at least one recess formed in said body configured to receive at least a portion of said at least one engagement member.

16. The device of claim 1, further comprising a handpiece at said proximal end of said device, said handpiece receiving a portion of said at least one arm, said handpiece further comprising:
- an actuator connected to said at least one arm and operable to control the motion of said at least one arm through at least one of a mechanical connection and an electronic connection; and
- at least one of a rotational adjustment mechanism and a translational adjustment mechanism that are independently selectable for operation;
- said rotational adjustment mechanism interconnecting said actuator and said at least one arm and configured to cause rotational motion of said at least one arm upon activation of said actuator;
- said translational adjustment mechanism interconnecting said actuator and said at least one arm and configured to cause translational motion of said at least one arm upon activation of said actuator.

17. The device of claim 16, wherein said rotational adjustment mechanism further comprises a first rotational gear attached to said actuator and a second rotational gear attached to said at least one arm, wherein rotation of said actuator is transferred through said first and second rotational gears to said at least one arm when said first and second rotational gears are engaged.

18. The device of claim 16, wherein said translational adjustment mechanism further comprises a translational gear attached to said actuator, a translational track within said handpiece, and a bridge interconnecting said translational track with said at least one arm, said translational gear and said translational track each having teeth, wherein rotation of said actuator causes said teeth of said translational gear to interlock with said teeth of said translational track and drive said translational track in a longitudinal direction when said translational gear and said translational track are engaged, and said bridge configured to transfer said longitudinal motion of said translational track to said at least one arm.

19. The device of claim 16, wherein said actuator is disposed about and movable along an axle to selectively engage and disengage said rotational adjustment mechanism and said translational adjustment mechanism.

20. The device of claim 16, wherein said rotational adjustment mechanism further comprises said at least one arm bonded to said actuator so that rotation of said actuator causes rotational motion of said at least one arm.

21. The device of claim 16, wherein said translational adjustment mechanism further comprises a slider having an elongate length in a longitudinal direction, said actuator selectively movable along said slider, said at least one arm bonded to said actuator so that movement of said actuator along said slider causes translational motion of said at least one arm in said longitudinal direction.

22. The device of claim 21, wherein said actuator further comprising:
- an actuator lumen extending through said actuator in fluid communication with a hollow lumen of said at least one arm; and
- an actuator channel disposed at least partially concentrically around said actuator lumen, said actuator channel configured to receive said slider therethrough.

23. The device of claim 22, wherein said actuator further comprising a key extending from said actuator and said slider further comprising a slot extending along at least a portion of a length of said slider, said slot configured to receive and slidably retain said key of said actuator.

* * * * *